US006402701B1

(12) United States Patent
Kaplan et al.

(10) Patent No.: US 6,402,701 B1
(45) Date of Patent: Jun. 11, 2002

(54) BIOPSY NEEDLE INSTRUMENT

(75) Inventors: Leopold S. Kaplan, Edison, NJ (US);
Lawrence J. Kelly, Fairfield; David L. Hamann, Cincinnati, both of OH (US)

(73) Assignee: FNA Concepts, LLC, Edison, NJ (US)

( * ) Notice: Subject to any disclaimer, the term of this patent is extended or adjusted under 35 U.S.C. 154(b) by 0 days.

(21) Appl. No.: 09/527,328

(22) Filed: Mar. 17, 2000

Related U.S. Application Data
(60) Provisional application No. 60/125,730, filed on Mar. 23, 1999.

(51) Int. Cl.[7] ................................................. A61B 5/00
(52) U.S. Cl. ...................................................... 600/567
(58) Field of Search ........................ 600/562, 564–567; 606/167, 170

(56) References Cited

U.S. PATENT DOCUMENTS

| 2,705,949 A | 4/1955 | Silverman ....................... 128/2 |
| 2,818,852 A | 1/1958 | Kugler ............................ 128/2 |
| 2,824,455 A | 2/1958 | Ristow et al. .................. 74/60 |
| 3,590,808 A | 7/1971 | Muller ......................... 128/2 B |
| 3,678,934 A | 7/1972 | Warfield et al. ............. 128/317 |
| 3,692,020 A | 9/1972 | Schied ........................ 128/2 B |
| 4,306,570 A | 12/1981 | Matthews .................... 128/754 |
| 4,314,560 A | 2/1982 | Helfgott et al. ............. 128/305 |
| 4,445,517 A | 5/1984 | Feild ............................ 128/752 |
| 4,461,305 A | 7/1984 | Cibley ........................ 128/754 |
| 4,489,724 A | 12/1984 | Arnegger ................ 128/303 R |
| 4,542,749 A | 9/1985 | Caselgrandi et al. ........ 128/752 |
| 4,605,011 A | 8/1986 | Näslund ...................... 128/752 |
| 4,644,952 A | 2/1987 | Patipa et al. ................ 128/305 |
| 4,705,038 A | 11/1987 | Sjostrom et al. ............ 128/305 |
| 4,723,545 A | 2/1988 | Nixon et al. ................. 128/305 |
| 4,763,667 A | 8/1988 | Manzo ........................ 128/750 |
| 4,768,504 A | 9/1988 | Ender ......................... 128/317 |
| 4,909,249 A | 3/1990 | Akkas et al. ................ 606/107 |
| 4,940,061 A | 7/1990 | Terwilliger et al. ......... 128/754 |
| 4,944,308 A | 7/1990 | Åkerfeldt .................... 128/751 |
| 4,986,827 A | 1/1991 | Akkas et al. ................ 606/107 |
| 4,989,614 A | 2/1991 | Dejter, Jr. et al. .......... 128/752 |

(List continued on next page.)

OTHER PUBLICATIONS

Mammotome HH, Ethicon Endo–Surgery, Inc. a Johnson & Johnson Company brochure Undated.
Fine Needle Aspiration, Kathleen M. Harris, M.D., FACR pp 101–105.
Breast Procedures, edited by D. David Dershaw pp 91, 94, 95.
General Ultrasound, Ed., Carol A. Mittelstaedt, M.D. p. 18.
Interventional Breast Ultrasonography, Ellen B. Mendelson, M.D. p. 57–76.
Thyroid and Parathyroid p. 107.

Primary Examiner—Max Hindenburg
(74) Attorney, Agent, or Firm—Kenyon & Kenyon

(57) ABSTRACT

An automated fine needle biopsy device is described for extracting tissue from the body predominantly in suspected cases of breast cancer. However, it can be used in other parts of the body accessible to needle biopsy. The device causes a fine needle, which is attached to the device, to reciprocate and/or rotate at the same time causing tissue to enter the needle. The depth and number of the thrusts can be pre-programmed, and the force behind each thrust is constant. Suction may or may not be used. The tissue extracted is subsequently expelled onto glass slides for microscopic interpretation. This device and method offer a vast improvement over the present method for fine needle biopsy wherein it is performed manually and in a very haphazard way. The prime deficiency of the manual method currently used is insufficient tissue extraction. This device will correct that situation enabling accurate diagnosis to be made on adequate tissue samples obtained. No similar device is known to be in clinical use at the present time.

48 Claims, 18 Drawing Sheets

U.S. PATENT DOCUMENTS

| | | | |
|---|---|---|---|
| 5,048,538 A | 9/1991 | Terwilliger et al. | 128/754 |
| 5,060,658 A | 10/1991 | Dejter, Jr. et al. | 128/753 |
| 5,108,400 A | 4/1992 | Appel et al. | 606/79 |
| 5,146,921 A | 9/1992 | Terwilliger et al. | 128/754 |
| 5,188,118 A | 2/1993 | Terwilliger | 128/753 |
| 5,201,749 A | 4/1993 | Sachse et al. | 606/177 |
| 5,240,011 A | 8/1993 | Assa | 128/751 |
| 5,241,969 A | 9/1993 | Carson et al. | 128/753 |
| 5,249,583 A | 10/1993 | Mallaby | 128/754 |
| 5,281,220 A | 1/1994 | Blake, III | 606/46 |
| 5,284,156 A | 2/1994 | Schramm et al. | 128/754 |
| 5,368,045 A | 11/1994 | Clement et al. | 128/754 |
| 5,392,790 A | 2/1995 | Kanner et al. | 128/753 |
| 5,415,169 A | 5/1995 | Siczek et al. | 128/653.1 |
| 5,415,182 A | 5/1995 | Chin et al. | 128/754 |
| 5,423,330 A | 6/1995 | Lee | 128/753 |
| 5,476,101 A | 12/1995 | Schramm et al. | 128/754 |
| 5,526,822 A | 6/1996 | Burbank et al. | 128/754 |
| 5,564,436 A | 10/1996 | Hakky et al. | 128/754 |
| 5,601,585 A | 2/1997 | Banik et al. | 606/180 |
| 5,609,602 A | 3/1997 | Machemer et al. | 606/171 |
| 5,618,295 A | 4/1997 | Min | 606/171 |
| 5,643,304 A | 7/1997 | Schechter et al. | 606/171 |
| 5,649,547 A | 7/1997 | Ritchart et al. | 128/754 |
| 5,820,312 A | 10/1998 | Stock et al. | 408/17 |
| 5,833,643 A | 11/1998 | Ross et al. | 604/22 |
| 5,871,493 A | 2/1999 | Sjostrom et al. | 606/180 |
| 5,916,229 A | 6/1999 | Evans | 606/171 |

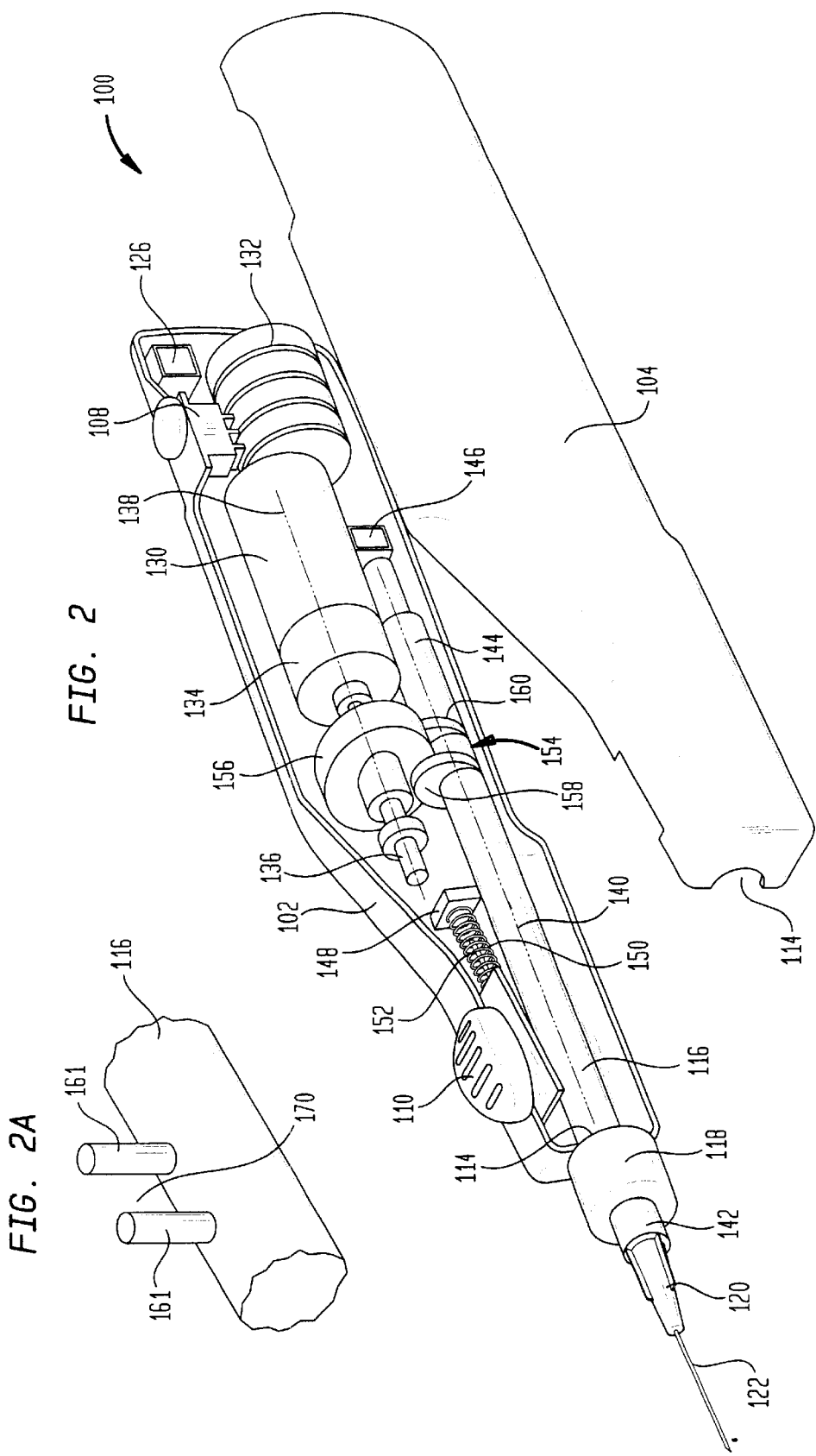

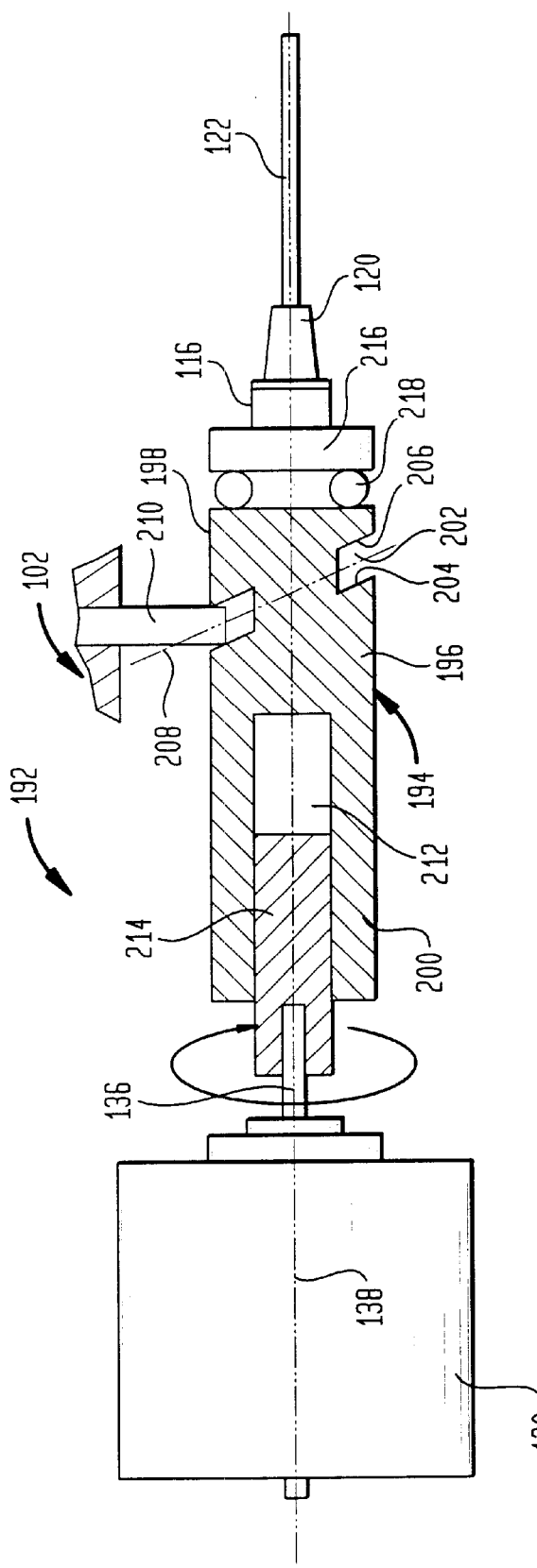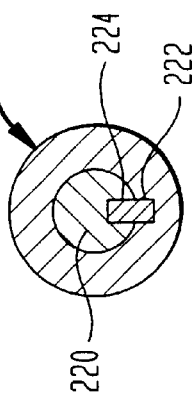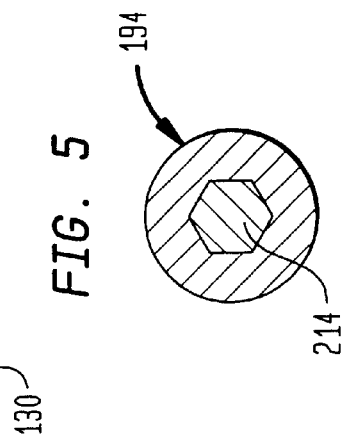

BIOPSY NEEDLE INSTRUMENT

The present application claims the benefit of U.S. Provisional Application No. 60/125,730, filed March 23, 1999, the disclosure of which is hereby incorporated by reference.

The present invention relates in general to the field of medical biopsy instruments, and more particularly, to such instruments for use in fine needle biopsy of human or animal tissue for medical diagnostics and the like.

BACKGROUND OF THE INVENTION

Biopsy instruments are often used to obtain tissue samples for microscopic examination to test for malignancy or other diseases and abnormalities. Generally, biopsies may be guided by either stereotactic means, CAT scan or ultrasound means. Image-guided biopsy procedures are particularly useful for non-surgical diagnosis of benign and malignant masses. The biopsy itself may be either a core biopsy or a fine needle aspiration biopsy. For example, an instrument for performing percutaneous biopsy procedures and collection of soft tissue is disclosed in Ritchant, et al., U.S. Pat. No. 5,649,547.

Other currently used biopsy instruments and methods include those disclosed in Siczek, et al., U.S. Pat. No. 5,415,169 and Assa, U.S. Pat. No. 5,240,011. Siczek, et al. and Assa each disclose a motorized biopsy needle positioner employed in a mammographic needle biopsy system for receiving coordinate information representative of an identified point of interest within the patient's captive breast under examination and automatically positioning a biopsy needle in accordance with the coordinate information to permit insertion of the biopsy needle to the identified point of interest.

Additionally, Clement, et al., U.S. Pat. No. 5,368,045 discloses a handheld biopsy needle instrument employing combined stylets and cannulas capable of taking multiple specimens while the other hand is free to manipulate an ultrasound probe. The stylet and cannulas are spring loaded, which upon firing, will penetrate the tissue for obtaining a biopsy specimen. A similar biopsy instrument having a plurality of stylets and cannulas which can be controlled independently for capturing a plurality of discreet specimens at a controlled depth is disclosed in Chin, et al., U.S. Pat. No. 5,415,182. See also Akerfeldt, U.S. Pat. No. 4,944,308.

Fine needle aspiration biopsy is often performed on a potentially malignant mass for confirmation of diagnosis prior to surgery, on more than one mass where multi-focal or multi-centric malignant disease is suspected, on a suspected benign lesion such as a fibroadenoma, where there is ambivalence about follow-up versus excision, or on an ultrasound imaged structure with features unlike a simple cyst. Among the benefits of fine needle aspiration when compared with other biopsy procedures are that it is less invasive, requires no incision, causes minimal discomfort, takes less time and costs considerably less. A discussion of fine needle aspiration is disclosed in the article Fine Needle Aspiration, Kathleen M. Harris, M. D., FACR, pp. 101–105.

Suction and capillary methods of aspiration have been successful on the breast. For suction aspiration, a syringe in a resting position is attached to a sampling needle. Suction is created by pulling the plunger of the syringe. In the capillary method, a syringe is not used and suction is not applied. With both methods, up to the present time the sampling needle is manually moved back and forth rapidly by the physician within the area to be studied. The needle is further angled in multiple directions to sample a cone-shaped area within the area to be studied. In the suction method, the suction should be maintained until material is visible in the plastic needle hub, or for a minimum of twenty up-and-down motions in varying directions. This method is described further in Interventional Breast Procedures, edited by D. David Dershaw, pp. 91, 94 and 95. A similar technique is described in General Ultrasound, Ed., Carol A. Mittelstaedt, M. D., pg. 18. The technique is also described in Interventional Breast Ultrasonography, Ellen B. Mendelson, M. D., pp. 57–76. Another similar technique is that discussed in Thyroid and Parathyroid, pg. 107.

Until now, and as described in the foregoing references, fine needle aspiration biopsies have been performed manually. Such a procedure involves manually thrusting a needle alone or a needle attached to a syringe, with or without suction. The procedure is generally random in that the depth of the thrusts, number of thrusts, the area covered and the force used are done in a very haphazard way. For example, one thrust could be 5 millimeters, while another could be 2 millimeters and so forth.

A significant limitation with random depth is that when a lesion is very small in diameter, there are occasions where none or a few of the thrusts obtain the necessary tissue sample. One of the thrusts may be directed to a lesion, but may bypass the lesion completely as a result of a lack of consistent direction of the thrusts. Random depth results in a significant amount of fine needle aspiration biopsies retrieving an insufficient amount of tissue with which to do an appropriate diagnostic evaluation. If the number of thrusts is limited, this compounds the problem further and increases the chances of missing the lesion.

Another limitation of the prior method is lack of significant thrusting energy. The force behind the thrust may be variable, and many may be insufficient enough to pierce the outer margins of certain lesions, especially fibroadenomas. The needle can potentially bounce off the fibroadenoma or push it aside rather than pierce the outer margin and obtain the necessary tissue.

Many fibroadenomas are currently surgically excised without any attempt to perform a fine needle biopsy. The cost of excisional biopsies are multiple times the cost of a fine needle aspiration biopsy. Significant medical financial resources could be saved by performing fine needle aspiration biopsies instead of excisional biopsies. Providing an improved method and an automated biopsy instrument for performing fine needle aspiration biopsies would reduce the need for excisional biopsies together with their inherent risks.

There is disclosed in Dejter, Jr., et al., U.S. Pat. Nos. 5,060,658 and 4,989,614 a medical instrument for fine needle aspiration biopsies of the prostate only. The biopsy instrument includes a needle having an opening which can be occluded by a stylet during both the penetration and withdrawal stage of an aspiration cycle during the biopsy procedure. After penetration of the target tissue, the needle is reciprocated a predetermined number of times as determined by the desired cytological sample yield. During the reciprocating procedure, the needle opening remains unoccluded by withdrawal of the stylet. Tissue sample is collected in a syringe under vacuum. After sufficient tissue sample has been collected, the stylet is returned to its forward position, thereby occluding the needle opening prior to withdrawal of the needle from the patient. The biopsy instrument is opened in order to remove the syringe containing the collected tissue sample for cytological analysis.

Naslund, U.S. Pat. No. 4,605,011 discloses a biopsy instrument for taking samples of cells of small tumors using fine needle puncturing techniques. The biopsy instrument includes a hand grip having a syringe provided with a removable cannula. The cannula is connected to a motor which is operative for driving the cannula in an oscillating, recipricatory motion. The motor is constructed as an electromagnet having pole elements, which when energized, cause reciprocal motion of a pole element which is coupled to the cannula. The cannula is connected to a container which is placed under vacuum for drawing a tissue sample from the cannula during the biopsy procedure. This instrument is not used without suction.

Patipa, et al., U.S. Pat. No. 4,644,952 discloses a surgical operating instrument provided with a needle which can be reciprocated by means of a cam and cam follower arrangement. The needle is attached to one end of a shaft, the other end supporting a laterally extending cam follower. The cam follower is captured interiorly within a cam between two opposing cam surfaces. The cam is rotated by a motor thereby effecting reciprocal motion of the needle. There is no stated use for the instrument disclosed in Patipa, et al.

The instruments disclosed in Dejter, Jr., et al., Naslund and Patipa, et al., although effecting reciprocal motion of the needle or cannula, have designs which provide disadvantages in fine needle biopsy procedures. For example, in certain cases the disclosed designs are complicated and therefore expensive to manufacture, do not provide accurate control of the reciprocal motion and thrust force required of fine needle biopsy procedures, are bulky or cumbersome in size making the instrument difficult to handle during the biopsy procedure, require the use of a stylet, or are not suitable for vacuum collection of a tissue sample. Similar disadvantages are known from a medical instrument which effects reciprocal motion of a needle by a rotating cam and spring arrangement. The cam is operative for advancing the needle in a forward direction, the return motion being effected by a compression spring.

There is accordingly the need for improvements in fine needle biopsy instruments which provide reciprocal and/or rotational motion of the needle to collect tissue samples for medical diagnostics in an accurate and efficient manner, while being suitable for use in various environments such as hospitals and the like.

SUMMARY OF THE INVENTION

The present invention broadly addresses the need for improved quality and completeness of technique, as well as an improved instrument for obtaining tissue samples through fine needle biopsy.

The present invention involves the use of fine needle biopsy techniques with a biopsy needle instrument that may be programmed to provide a predetermined depth and number of thrusts, a predetermined thrust cycle, a predetermined pattern and/or area to be covered, and a predetermined force of thrust. By manually changing slightly the angle of the device with the needle, multiple areas of the tumor can be sampled in a very short period of time. The needle or syringe is attached to a small handheld device, which can be driven by a small electric motor or hydraulic fluid, e.g., compressed air and the like. The needle can move in a "jackhammer" type fashion to implement the programmed settings for depth, number, cycles and force of thrusts. The force behind each thrust could be constant and of sufficient magnitude to pierce the outer margin of a small lesion such as a fibroadenoma rather than pushing them aside because of insufficient force. The device can be used with or without suction for aspiration of the tissue sample. Since all the functions of the instrument can be predetermined and preprogrammed, the physician can start the procedure, focus on the ultrasound monitor and then position the needle in juxtaposition to the lesion. The invention also incorporates a safety mechanism or "deadman switch" to prevent accidental initiation of the reciprocal action of the needle prior to the actual biopsy.

The fine needle aspiration biopsy instrument in accordance with the present invention generally includes a powered handpiece, a biopsy needle to be inserted into the handpiece, an internal programmable controller or remote programmable computer for controlling the instrument, a power source for operation of the instrument and a suction source. As will be understood from a further description of the present invention, the suction connection is an optional feature.

The instrument to which the biopsy needle is attached is operative to provide at least one, and preferably two motions to the biopsy needle. Specifically, the instrument incorporates a jack-hammer type motion that causes a reciprocal thrusting motion of the biopsy needle into the tissue to be biopsied, and optionally, a rotary motion of the biopsy needle which will produce a cutting effect.

The power source is operative for providing the necessary power for operating the instrument to affect the reciprocal and/or rotary type motion of the biopsy needle by means of, for example, an electric or pneumatic operated motor for operation of a reciprocating/rotating assembly as disclosed pursuant to the present invention. In addition to the thrusting or reciprocal motion, the biopsy needle may also be rotated or manipulated about an orbital pattern as opposed to rotation along its longitudinal axis, which is also contemplated pursuant to the present invention. Further in this regard, a suitable cam assembly or other such mechanism can be inserted into the handpiece to affect orbital rotation of the biopsy needle in a predetermined pattern, for example, oval, circular, random, zig-zag, rectangular and the like. In use, the thrusting action of the biopsy needle will orbit such that the pattern of specimens taken of the tissue sample will correspond to the predetermined pattern defined by the cam assembly or other such mechanism in the instrument. It is therefore possible for the instrument to sample the tissue at a plurality of random or predetermined locations to ensure that the area from which specimens are to be taken is adequately sampled.

The programmable controller or computer may be set according to the desired parameters either before or after insertion of the needle into the patient. When the physician is ready for the sample to be taken, he or she may activate the instrument by turning a switch that controls the power source, e.g., electricity or hydraulic source. As the sample is being taken, the physician is free to focus on the ultrasound monitor which will demonstrate the lesion together with the needle within it. By focusing on the monitor, this ensures that the tissue extracted is from the lesion itself and not from the surrounding tissues.

A programmable device for use in association with the instrument permits programming of the depth of thrusts, the number of thrusts per unit of time, the area or pattern of thrusts, the force of the thrusts, as well as other variable options to specifically select desired parameters. A programmable device may be provided within the handpiece itself or may be remote therefrom such as using a programmable computer.

By way of one illustrative example, the biopsy needle used for fine needle aspiration may range from 20 gauge to 25 gauge, having a 4.0 mm stroke length, a zigzag area pattern, e.g., 2–6 mm travel between thrusts and 10–20 strokes per second for 5 seconds. The biopsy needle may be connected to the handpiece using a special T-connector which is described in this application on pages 28 to 29.

It can be appreciated from the foregoing description of the biopsy needle instrument in accordance with the present invention, that the physician can program the instrument to accommodate any specific tissue or lesion to be biopsied with a number of variable parameters to ensure that sufficient samples of tissue for biopsy are obtained. Once the specimen has been obtained, with or without suction, into the biopsy needle, the specimen can be extracted into a jar of preservative fluid or onto a slide for analysis.

In accordance with one embodiment of the present invention there is described a medical instrument comprising a housing having an opening at one end thereof; a first shaft within the housing for reciprocal motion, the first shaft having a front section and a rear section, the front section of the shaft extending adjacent the opening in the housing; a cam assembly within the housing, the cam assembly comprising first and second cam followers arranged in spaced apart relationship on the first shaft, a cam arranged between the first and second cam followers mounted on a rotatable second shaft, the cam having outwardly facing first and second cam profiles respectively engaging an opposing one of the first and second cam followers, whereby the cam assembly upon rotation of the cam converting rotating motion of the second shaft to reciprocal motion of the first shaft.

In accordance with another embodiment of the present invention there is described a medical instrument comprising a housing having an opening at one end thereof; a reciprocating shaft within the housing, the reciprocating shaft having a front section and a rear section, the front section of the shaft extending outwardly through the opening; a cam assembly within the housing operatively coupled to the reciprocating shaft, the cam assembly comprising a cam having first and second spaced apart outwardly facing cam profiles, a first cam follower on one side of the cam in engagement with the first cam profile, and a second cam follower on the other side of the cam in engagement with the second cam profile; and a motor operatively coupled to the cam for rotational movement of the cam, whereby the engagement of the first and second cam profiles with the first and second cam followers during rotation of the cam causes reciprocal movement of the reciprocating shaft.

In accordance with another embodiment of the present invention there is described a medical instrument comprising a housing having an opening at one end thereof; a reciprocating shaft along a first axis within the housing, the reciprocating shaft having a front section and a rear section, the front section of the shaft extending outwardly through the opening; a cam assembly within the housing comprising a cam having first and second spaced apart cam profiles, a first cam follower on one side of the cam in engagement with the first cam profile, and a second cam follower on the other side of the cam in engagement with the second cam profile; and a motor on a second axis within the housing operatively coupled to the cam for rotational movement of the cam, the second axis offset from the first axis, whereby rotation of the cam causes reciprocal movement of the reciprocating shaft.

In accordance with another embodiment of the present invention there is described a medical instrument comprising a housing having an opening at one end thereof; a shaft within the housing for reciprocal motion, the shaft having a front section and a rear section, the front section of the shaft extending outwardly through the opening of the housing; a motor within the housing; and a cam assembly within the housing comprising a cam operationally coupled to the motor for rotational movement of the cam, the cam having a track and a cam follower fixed to the housing and received within the track; whereby receipt of the cam within the track during rotation of the cam by the motor causes reciprocal movement of the shaft.

BRIEF DESCRIPTION OF THE DRAWINGS

The above description, as well as further objects, features and advantages of the present invention will be more fully understood with reference to the following detailed description of a biopsy needle instrument, when taken in conjunction with the accompanying drawings wherein:

FIG. 2 is an exploded perspective view of the needle biopsy instrument showing its component parts including a cam assembly in operative assembled relationship;

FIG. 2A is a perspective view of a pair of pins designed as cam followers in accordance with one embodiment of the present invention;

FIG. 4 is a diagrammatic illustration of a needle biopsy instrument constructed in accordance with another embodiment of the present invention;

FIG. 5 is a cross-sectional view taken along line 5—5 in FIG. 4 showing a coupling arrangement;

FIG. 6 is a cross-sectional view showing a coupling arrangement constructed in accordance with another embodiment of the present invention;

DETAILED DESCRIPTION OF THE PREFERRED EMBODIMENTS

Figure 1:
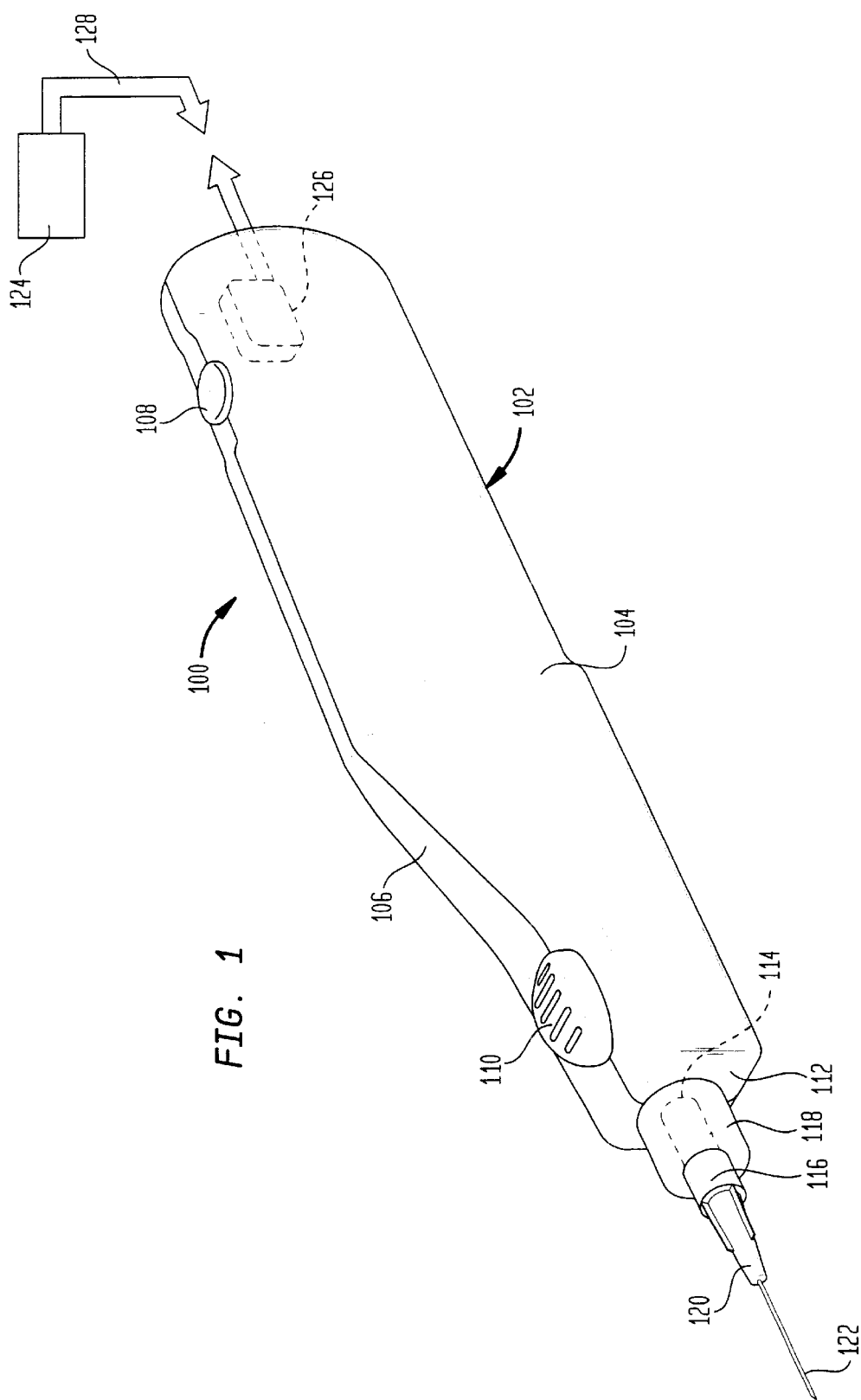
FIG. 1 is a perspective view of a needle biopsy instrument constructed in accordance with one embodiment of the present invention.

One of the most dreaded diseases in the world today is breast cancer. In this country alone, there are over 200,000 new cases diagnosed every year, and there are approximately 45,000–50,000 deaths per year. The optimum chance for survival depends upon early detection, diagnosis and treatment. The best method of detection is mammography. Diagnosis depends upon biopsy, and treatment consists mainly of surgery, chemotherapy and radiation therapy.

There are four methods of biopsy—surgical excision, stereotactic large core biopsy, large core biopsy "guns" and fine needle biopsy with or without suction.

There are approximately 1–1.2 million breast biopsy procedures performed per year in this country alone. Approximately 80–90% of them turn out to be benign. With this in mind, it should be the goal of any biopsy procedure to provide as accurate a diagnosis as possible. In addition, it should be as minimally traumatic to the patient as possible, and as least expensive as possible. The biopsy procedure that addresses these matters the best is fine needle biopsy. Surgical excision means a surgical procedure with anesthesia, skin incisions, and patient morbidity. It is the most expensive of the biopsy procedures. Stereotactic and large core biopsy gun procedures utilize large needles, some as large as 11 gauge, as well as anesthesia, skin incisions and patient morbidity.

Fine needle biopsy, with or without suction, can provide an accurate diagnosis. It is almost completely atraumatic with very little, if any, patient morbidity. It does not require anesthesia. There is no skin incision. It takes only one needle insertion through the skin. The needle size ranges between 20–25 gauge. The procedure is very rapid, 5 to 10 minutes at most. It is the least expensive of the biopsy procedures, and the diagnosis should be available the day following the procedure. As an example, a woman could have a diagnostic or screening mammogram on a certain day. If a lesion is found, it can be biopsied the same day, and she can have an answer the following day. At the present time, she may have to wait weeks between the mammogram and the answer to a biopsy procedure.

At the present time, FNA or fine needle aspiration biopsies are performed manually. This involves the manual thrusting of a needle alone or a needle attached to a syringe with or without suction. This is a random procedure in that the depth of the thrusts and the area to be biopsied are done in a very haphazard way. For example, one thrust could be 8 mm, another 1.5 cm, another 4 mm and another 1.5 mm. The lesion may be only 5–6 mm in diameter, and it is possible that only 20–30% or even less of the thrusts may actually obtain tissue. The biggest deficiency of fine needle biopsy as it exists up to now is the lack of sufficient tissue extracted. Therefore, lack of consistent direction and depth is a major deficiency of the present procedure. A second problem up to now is the lack of consistent and sufficient thrusting force. The wide variability in thrusting force could lead to the inability of the needle to pierce the outer margins of certain lesions such as fibroadenomas. The needle may bounce off of the fibroadenoma or push it aside and, as such, no tissue may be extracted.

The purpose of the proposed biopsy device is to perform fine needle biopsies with a programmable device whereby the depth of the thrusts are pre-determined and controlled. In addition, the force behind each thrust is constant and sufficient to pierce the outer margins of certain lesions such as fibroadenomas rather than pushing them aside. Other options would include a rotatory motion of the needle to produce a cutting effect as well as a pre-programmed area pattern to be biopsied such as a circular or zigzag pattern.

The needle or syringe would be attached to a small hand-held device. The device would function similar to a jackhammer, producing rapid oscillatory thrusts of the needle. Multiple thrusts would be accomplished with pre-programmed depth settings and possible pre-programmed patterned areas. For example, a series of 10–20 thrusts could be performed directed at one point, or a series of 20 thrusts or even 50 thrusts could be directed in a circular pattern. The thrusts could be programmed to travel 2 mm, 4 mm, 6 mm, whichever one chooses. There may be suction or no suction.

A general description of the actual procedure is as follows. A mass in the breast is identified by ultrasound. A fine needle attached to the device is now introduced into the breast under ultrasound guidance. The needle is advanced to the lesion, and the tip of the needle pierces the outer rim of the lesion. The device is now activated, and a series of 10–20 thrusts/second is accomplished for 2–3 seconds. The device is now angled slightly while still in the lesion, and the device is activated again for 2–3 seconds. This can be done 4–5 times so that the whole lesion is biopsied. The needle and device are then removed from the breast. The tissue is extracted from the needle, put on a slide and sent to the pathologist or cytologist for interpretation. The whole procedure should take no more than 5–10 minutes. There is no incision, no anesthesia, and no morbidity to speak of.

At the present time, stereotactic biopsies are performed in a pre-programmed direction and depth, by only one thrust is made at a time with removal of multiple large cores. The original stereotactic unit costs $225–$250,000. One needs a dedicated room, technicians and nurses. It also utilizes X-rays to localize the lesion. Biopsy guns use large core needles, and anesthesia is necessary. As stated already, only one thrust is accomplished at each "firing" of the gun.

As stated in many articles on needle biopsy procedures, any solid lesion that could be visualized with ultrasound should be biopsied with a fine needle. Calcifications, a possible sign of malignancy, cannot be seen adequately with ultrasound and should therefore be biopsied with large-gauge biopsy devices.

Many fibroadenomas, which are benign lesions, are now surgically excised without any attempt at needle biopsy. The cost of an excisional biopsy is many times the cost of a fine needle biopsy. Millions of medical dollars could be saved performing fine needle biopsies instead of excisional biopsies. This could be accomplished if fine needle biopsies are made reliable. An automated fine needle biopsy device will greatly enhance the reliability of fine needle biopsies.

The most common application will be for breast lesions, but it should be understood that the device can be used wherever fine needle biopsies are now performed, including chest, abdomen, pelvis, neck (thyroid), axilla, etc. It can also be utilized in veterinary medicine.

In summary, the most common deficiency with fine needle biopsy up to the present is insufficient tissue extraction. The automated fine needle biopsy device as described pursuant to the present invention will correct that problem. The procedure is rapid, cost effective, almost completely without morbidity, and when adequate tissue is obtained, a diagnosis will be possible in virtually every case.

There is no similar device in use today for doing fine needle biopsies. Stereotactic and large-core biopsy guns have many drawbacks as outlined. By automating the fine needle biopsy procedure that is now done manually, it is felt that the shortcomings of this procedure as performed up to now will be corrected. As a result of this, the reliability of this procedure can be assured.

In describing the preferred embodiments of the subject matter illustrated and to be described with respect to the drawings, specific terminology will be utilized for the sake of clarity. However, the invention is not intended to be limited to the specific terms so selected and is to be understood that each specific term includes all technical equivalents which operate in a similar manner to accomplish a similar purpose.

Referring now to the drawings, where like reference numerals represent like elements, there is shown in FIG. 1 a perspective view of a needle biopsy instrument designated generally by reference numeral 100. The instrument 100 is constructed from an elongated housing 102 having a right half 104 and a left half 106. Extending outwardly through the housing 102 at one end thereof is a master on/off switch 108. In a similar manner, a "deadman" switch 110 extends outwardly from the housing 102 at the other end thereof. The forward end 112 of the housing 102 is provided with an opening 114 through which there extends an elongated shaft 116. The opening 114 is covered by a flexible boot 118 through which the shaft 116 extends. The boot 118 can be constructed of suitable polymer materials well known in the medical instrument art. A coupling device 120 is attached to the end of the shaft 116 for releasably securing a needle 122 thereto. In the preferred embodiment, the coupling device 120 is integrally formed as one unit with the needle 122 for attachment to the instrument 100. In the preferred embodiment, the needle 122 which will be used for fine needle biopsy procedures, will preferably have a size in the range of about 20–25 gauge. However, other size needles may be used with the instrument 100 of the present invention. The instrument 100 may be connected to a remote computer 124 and/or be provided with an internal programmable microprocessor 126 for operation of the instrument 100. The microprocessor 126 can be connected to the computer 124 using any similar data link 128.

Referring to FIG. 2, the instrument 100 includes a motor 130 which may be electric or hydraulic. In the case of hydraulic, the motor 130 may be driven by an air or liquid feed supply (not shown) which can be external to the housing 102 or provided internally by means of, for example, a compressed air source. In the illustrated embodiment, the motor 130 is in the nature of an electric motor which is powered by a battery source 132. The battery source 132 may be in the nature of rechargeable batteries, or conventional disposable batteries. Also, the power source can be household AC voltage or DC voltage through use of a converter. In either event, the battery source 132 is operative of the motor 130. The motor 130 is of known design in the medical instruments field, for example, those having rpm in the range of about 200–2000, which can provide 20 strokes in the range of 0.6–6 seconds. It is to be understood that the foregoing particulars of the motor 130 are by way of example only, and other rpm's and stroke frequencies may be incorporated into the instrument 100 in accordance with the present invention.

The motor 130 may include a gear box 134 to provide the desired rotational speed and torque for use in the instrument 100. The motor 130 via the gear box 134, is operative for rotation of a shaft 136 coupled thereto. The motor shaft 136 is rotated along its longitudinal axis 138.

Shaft 116 extends longitudinally through the housing 102 underlying motor shaft 136 and a portion of the motor 130. The shaft 116 has its longitudinal axis 140 arranged parallel to the longitudinal axis 138 of motor shaft 136. Shaft 116 is slidably mounted within the housing 102 using any suitable means, such as bearing supports (not shown), molded portions of the housing 102 and the like. The shaft 116 may have a rectangular cross section along all or a portion thereof to preclude its rotation within the housing 102, or a circular cross section throughout where rotation of the shaft is desired during operation of the instrument 100. A front section 142 of the shaft 116 extends outwardly through opening 114 to which the coupling device 120 is attached. A rear section 144 of the shaft extends underlying the shaft 136 where it terminates adjacent a reciprocating shaft positioning switch 146. Other switches within the instrument 100 include a momentary actuator switch 148 which is coupled to the deadman switch 110 by means of a push rod 150 and compression spring 152. A discussion of the deadman switch 110, positioning switch 146 and momentary actuator switch 148 will be described hereinafter.

A cam assembly 154 is positioned within the housing 102, coupling shaft 136 to shaft 116 at the rear section 144. As further shown in FIGS. 3A and 3B, the cam assembly 154 includes a cam 156 and first and second cam followers 158, 160. The cam 156 is constructed in the nature of a cylindrical body 162 having spaced apart surfaces defining outwardly facing first and second cam profiles 164, 166. The body 162 of the cam 156 is mounted to shaft 136 by means of a cylindrical member 168. From the foregoing description, rotation of shaft 136 by means of motor 130 and gear box 134 will cause cam 156 to rotate about axis 138.

The first and second cam followers 158, 160 are mounted to the shaft 116. By way of example, each of the cam followers 158, 160 are in the nature of flat disks or preferably elongated cylindrical pins 161, see FIG. 2A which project upwardly in a generally radial direction from the shaft 116 toward cam 156. The spaced apart cam followers 158, 160 define an opening 170 therebetween which is sized to receive a peripheral portion of the cam 156. Cam follower 158 is operative for engagement with the first cam profile 164, while the second cam follower 160 is operative for engagement with the second cam profile 166. It is to be understood that the cam followers 158, 160, can be any other shaped body which extends outwardly from shaft 116 for engagement with the first and second cam profiles 164, 166. In this regard, the cam followers 158, 160 can be separately mounted elements or integrally formed with the shaft 116.

Figure 3A:
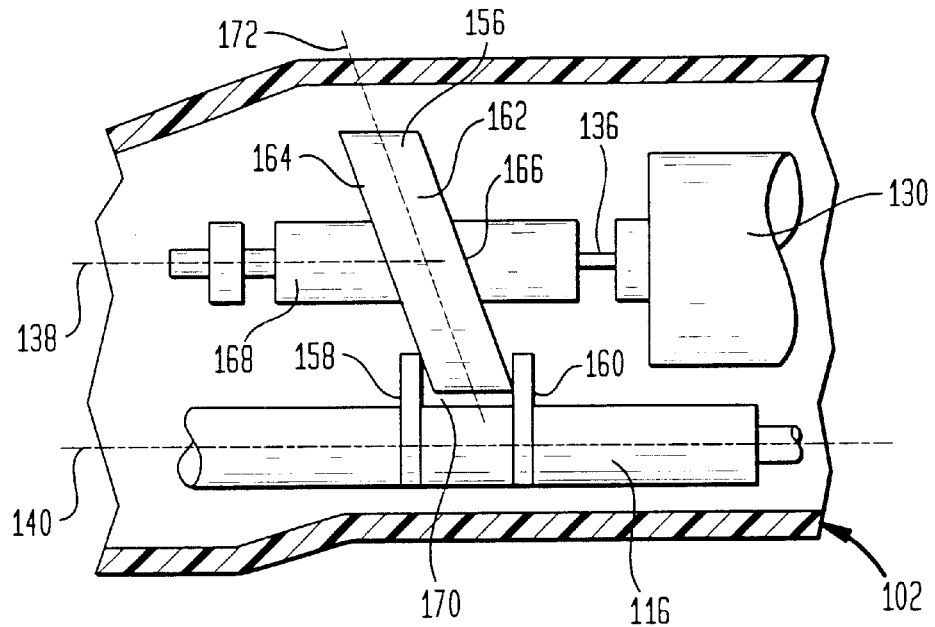
FIGS. 3A and 3B are front elevational views showing the cam assembly in sequential operative positions for effecting reciprocal motion of the needle carrying shaft.
Figure 3B:
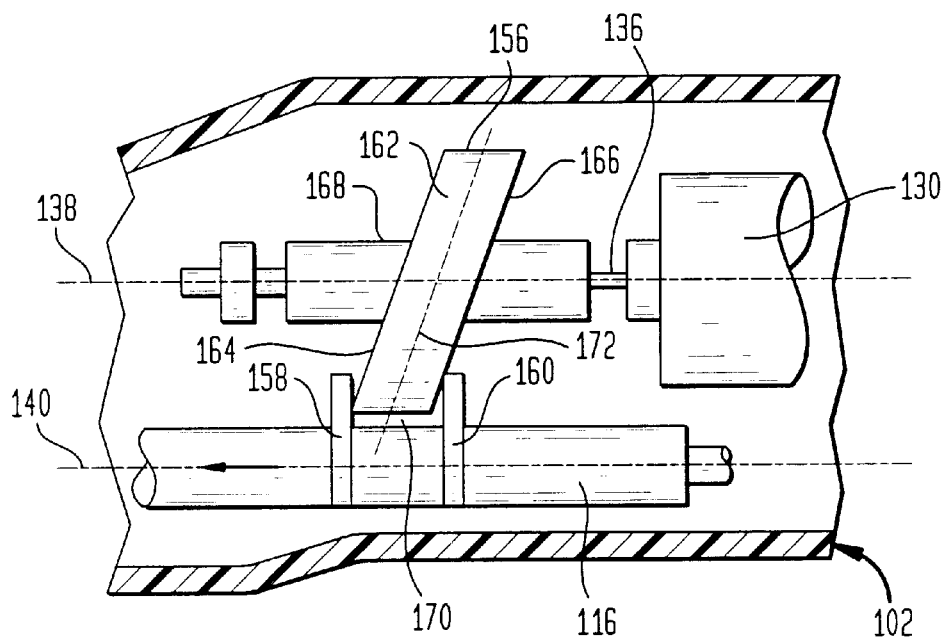

As shown in FIGS. 3A and 3B, upon rotation of the cam 156 by operation of motor 130, the shaft 116 will be caused to reciprocate as the cam followers 158, 160 ride in engagement with the first and second cam profiles 164, 166. By altering the first and second cam profiles 164, 166, various movements can be effected with respect to the shaft 116. For example, the stroke length of the shaft 116 can be changed by changing the angular relationship between the longitudinal axis 172 of the cam 156 with respect to its rotational axis 138. In this regard, the greater the angle between axes 138, 172, the greater the stroke length will be produced on the shaft 116. A maximum stroke length in the range of about 1 cm is contemplated for the instrument 100. However, it is to be understood that other stroke lengths can be used in biopsy needle instruments 100 in accordance with the present invention.

Figure 12:
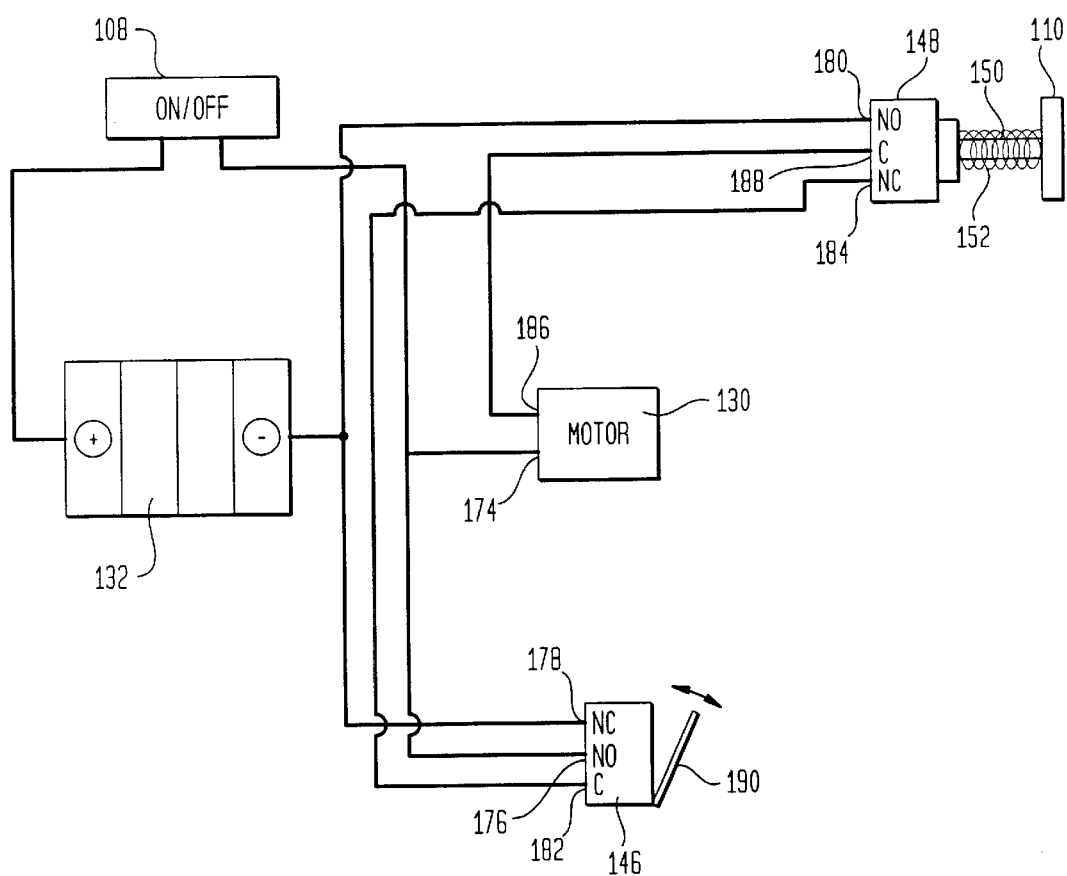
FIG. 12 is a schematic illustration of one embodiment of an electronic control circuit for operation of the needle biopsy instrument.

Referring now to FIG. 12, there is illustrated a schematic drawing of one electronic control circuit for operation of the instrument 100, the bold circuit lines representing the dynamic brake circuit for shaft positioning. One side of the on/off switch 108 is connected to the positive terminal of battery source 132. The other side of the on/off switch 108 is connected to terminal 174 on motor 130 and to terminal 176 on the positioning switch 146. Terminal 176 is a normally open position of the positioning switch 146. The negative side of the battery source 132 is connected to terminal 178 on the positioning switch 146 and to terminal 180 on the momentary actuator switch 148. Terminal 178 corresponds to a normally closed position on the positioning switch 146, while terminal 180 corresponds to a normally open position of the momentary actuator switch 148. Closed terminal 182 on the positioning switch 146 is connected to normally closed terminal 184 on the momentary actuator switch 148. Terminal 186 of the motor 130 is connected to terminal 188 on the momentary actuator switch 148, corresponding to a closed position. The momentary actuator switch 148 is coupled to the deadman switch 110 by means of push rod 150 and compression spring 152.

In operation, the deadman switch 110 is closed by depressing same manually so as to cause push rod 150 to close the connection between terminals 180, 188. At the same time, the operator having actuated the on/off switch 108 will allow power from battery source 132 to be fed to the motor 130 for its operation. In the event of release of the deadman switch 110, compression spring 152 will urge push rod 150 away from engagement with the deadman switch 148 to open the connection between terminals 180, 188. However, power to the motor 130 is still provided after release of the deadman switch 110, through positioning switch 146, until the shaft 16 is in a "home" position.

The positioning switch 146 is positioned within the housing rearwardly of the shaft 116. The positioning switch 146 has an actuating lever 190. In the event of a malfunction of the instrument 100, whereby the stroke length of the shaft 116 is outside a predetermined acceptable range, the shaft will engage lever 190 so as to open the positioning switch 146. Normally, the positioning switch 146 is in a closed position providing electrical continuity between terminals 178, 182 so as to close the circuit upon actuation of the momentary actuator switch 148 by means of the deadman switch 110. In the event that the positioning switch 146 is activated by movement of lever 190, the positioning switch will open thereby disconnecting power to the motor 130. The positioning switch 146 thereby functions as a safety switch to preclude injury to a patient. In this regard, the positioning switch 146 provides a home position for the shaft 116 to ensure that the first thrust of the shaft is outward away from the instrument 100, as opposed to being retracted within the instrument. As can be appreciated by the foregoing description, actuation of the motor 130 will effect rotation of cam 156 to cause reciprocal motion of the shaft 116 as the cam followers 158, 160 engage the first and second cam profiles 164, 166. In the event that the deadman switch 110 is inactivated by releasing same, and that activation of the positioning switch 146 occurs, the motor 130 will stop operation. Thus, both the deadman switch 110 and the positioning switch 146 control the motor 130. In order for the motor 130 to shut off, the deadman switch 110 must be released and the positioning switch 146 must be actuated.

The instrument 100 may operate in a manual mode, in an on and off fashion, with continued reciprocation of the shaft 116. The instrument 100 may also be operated under programmed control according to the desired parameters selected by the physician. For example, by programming the instrument 100, this permits predetermination of the number of thrusts, the number of thrusts per unit of time, as well as other variable options to specifically select desired parameters. The programmable aspect of the instrument 100 may be achieved by means of a programmed external computer 124 and/or an internal microprocessor 126. In addition, the computer 124 and/or microprocessor 126 may store critical patient data as well as other diagnostic information.

Referring now to FIGS. 4–6, another embodiment of a needle biopsy instrument 192 will now be described wherein like reference numerals represent like elements. A cam 194 is constructed from an elongated body 196 having a front section 198 and a rear section 200. The front section 198 is provided with a circumferential opening which forms a cam track 202 between adjacent sidewalls 204, 206 of the opening. The axis 208 is arranged at an angle to the longitudinal axis 138 of shaft 136 about which the cam rotates. In other words, the cam profile formed by sidewalls 204, 206 and hence the cam track 202, is arranged at an angle to its axis of rotation. A cam follower 210 is attached to the housing 102 and extends into the cam track 202. The cam follower 210 may be constructed as a projection or pin from the housing 102 having its free end captured within the opening forming the cam track 202.

The rear section 200 of the cam 194 is provided with elongated internal bore 212. The bore 212 is sized and configured to slidingly receive a coupling 214 which is attached to shaft 136. The coupling 214 and bore 212 are provided with other than a circular shape, such as square, triangular, polygonal, oval or the like such that rotation of the coupling will effect rotation of the cam 194. In this regard, upon rotation of the coupling 214 by means of the motor 130, the rotary motion will be transmitted to effect rotation of the cam 194. As the cam follower 210 is captured within the cam track 202, rotation of the cam 194 will cause reciprocal motion of the cam. This reciprocal motion is transmitted to the needle 122 which is attached to coupling device 120. The coupling device 120 is attached to shaft 116 which is supported on a support member 216. To prevent rotation of the support member 216, and hence the needle 122, the support member is maintained in contact with cam 194 by an intervening bearing 218. The bearing 218 will permit rotational motion of the cam 194, while facilitating the prevention of rotational motion of the support member 216. In this regard, the support member 216 and adjacent housing 102 will be provided with a guide pin and linear track arrangement as to be generally described with respect to the FIG. 6 embodiment. This, in turn, will prevent the support member 216 from rotating, while at the same time, permitting its reciprocal movement.

In an alternate embodiment as shown in FIG. 6, the coupling 220 may be in the nature of a cylindrical body which transmits rotational motion to the cam 194 by means of an elongated key 222. The bore 212 in the cam 194 will also be of cylindrical shape. The key 222 is received within an elongated opening 224 within the coupling 220. As a result, the coupling 220 can slide longitudinally within the bore 212, while transmitting rotation of the coupling to the cam 194 as a result of the interlocking key 222.

Figure 7:
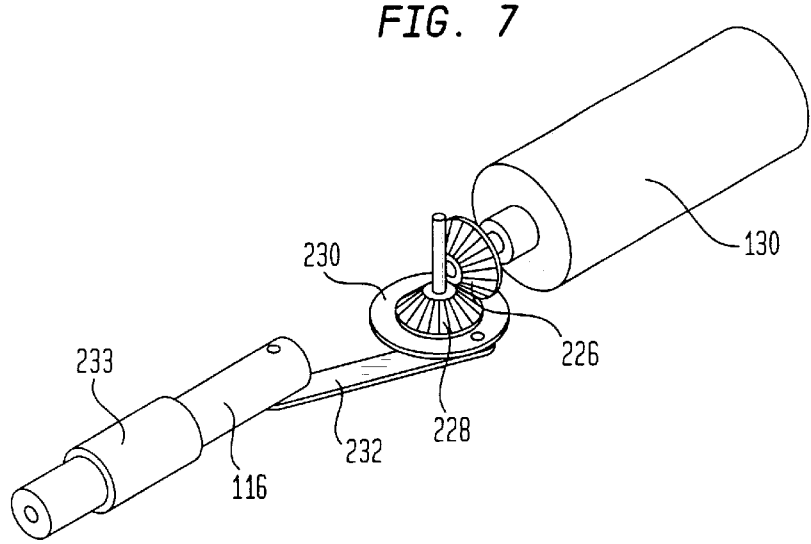
FIG. 7 is a perspective view of a reciprocating assembly for use in the needle biopsy instrument constructed in accordance with another embodiment of the present invention.
Figure 8:
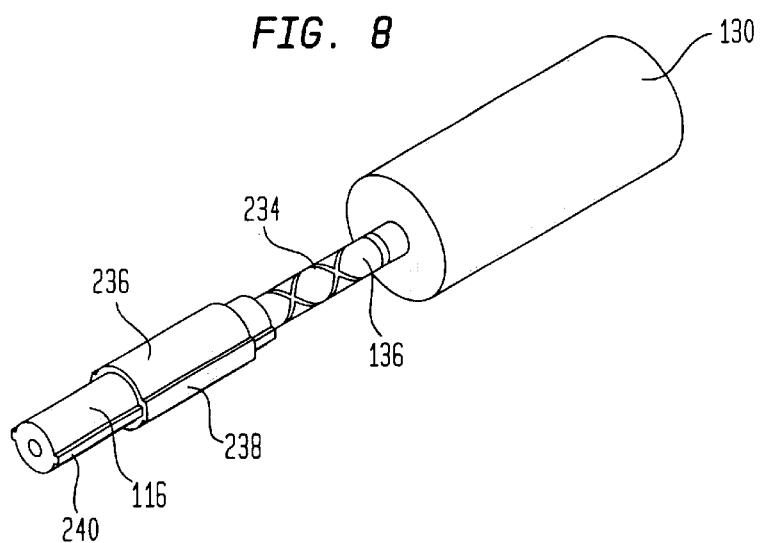
FIG. 8 is a perspective view of a reciprocating assembly for use in the needle biopsy instrument constructed in accordance with still another embodiment of the present invention.
Figure 9:
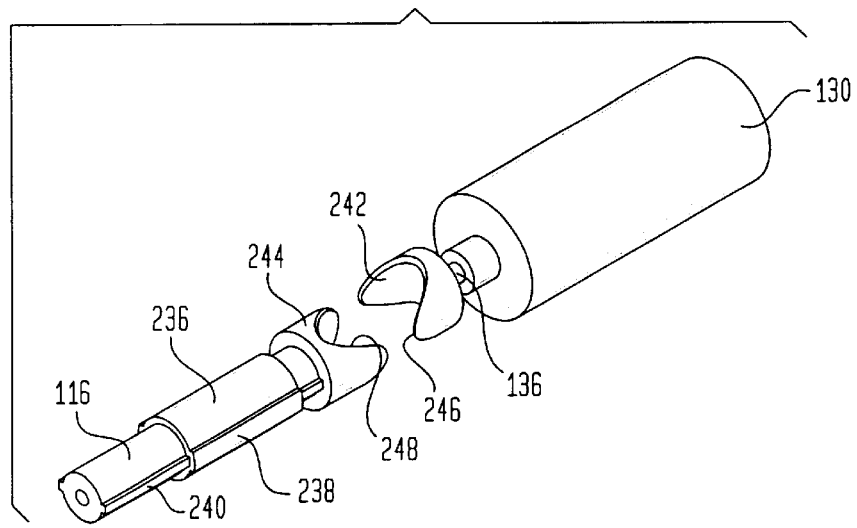
FIG. 9 is a perspective view of a reciprocating assembly for use in the needle biopsy instrument constructed in accordance with yet still another embodiment of the present invention.

Referring now to FIGS. 7–9, there will be described alternative assemblies for use in the instrument 100 for effecting reciprocal motion of the needle 122. As shown in FIG. 7, motor 130 is coupled to a first beveled gear 226 which is meshed with a second beveled gear 228. The second beveled gear 228 is supported on a plate 230 which is coupled to a push rod 232 attached to a peripheral portion of the plate. The push rod 232, in turn, is connected to one end of the shaft 116. By rotation of the first and second beveled gears 226, 228, the push rod 232 will effect reciprocal motion of shaft 116. The shaft 116 slides freely within a stationary sleeve 233 which is supported within the housing 102.

Referring now to FIG. 8, the shaft 136 is provided with a continuous helical groove 234 or gear. The shaft 136 is received within a bore (not shown) extending within one end of the shaft 116. The end of the shaft 116 is provided with suitable means for tracking within the helical groove 234 or engagement with the gear to effect reciprocal motion of the shaft. Shaft 116 is slidingly received within a stationary sleeve 236 which is provided with outwardly extending elongated projections 238. The projections 238 are captured within a corresponding portion of the housing 102 to prevent rotation of the stationary sleeve 236. The shaft 116 is provided with similar shaped side projections 240 which are slidingly received within the interior opening formed by side projections 238 formed within sleeve 236. Based upon this arrangement, shaft 116 will reciprocate freely within sleeve 236 while being precluded from rotation by the presence of the side projections 240.

Turning now to FIG. 9, a pair of C-shaped cam members 242, 244 are respectively attached to shafts 136, 116. The C-shaped cams 242, 244 have respective cam surfaces 246, 248 which are held in contact with each other when in assembled relationship by means of, for example, a spring (not shown). By rotation of the C-shaped cam 242, its cam surface 246 will track the cam surface 248 on C-shaped cam 244 causing reciprocal motion of shaft 116.

Figure 10:
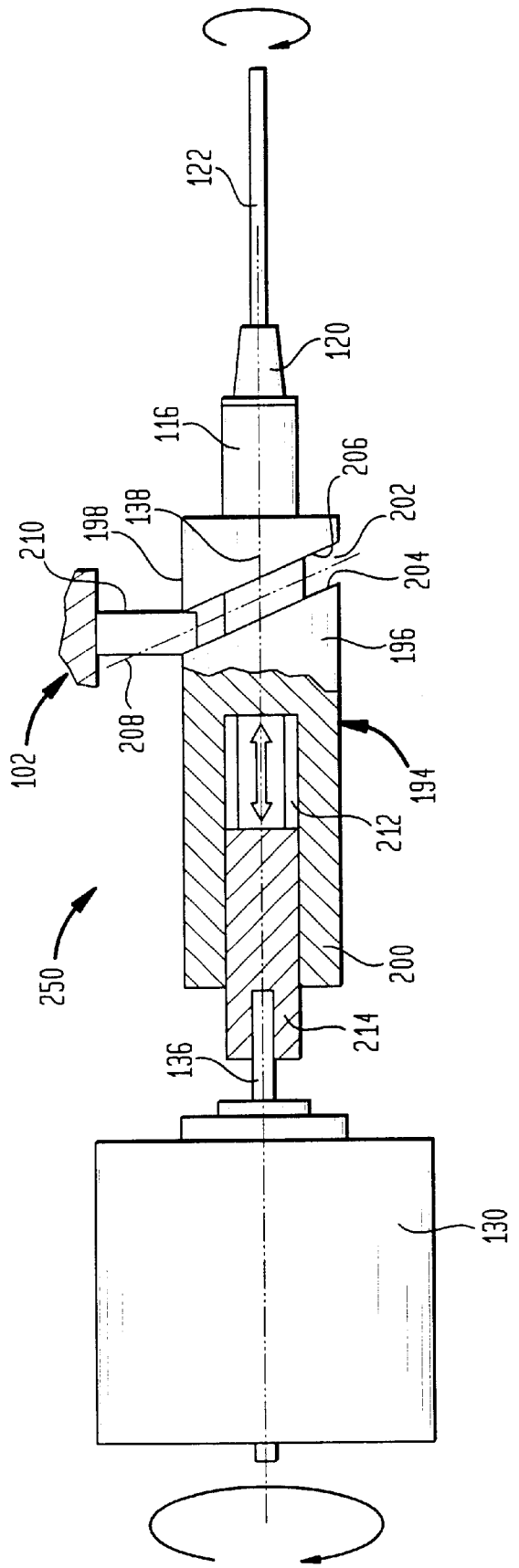
FIG. 10 is a diagrammatic illustration of a needle biopsy instrument constructed in accordance with another embodiment of the present invention.

As thus far described, the biopsy needle instrument of the present invention provides reciprocal motion to the attached needle 122. It may also be desirable that the needle 122 be simultaneously rotated during its reciprocal motion. Turning to FIG. 10, a needle biopsy instrument 250 of similar construction to instrument 192 as shown in FIG. 4 is illustrated. The instrument 250 provides both reciprocal and rotational motion of shaft 116. In the instrument 250, the shaft 116 is attached to the front section 198 of the cam 194. As previously described with respect to the instrument 192 of FIG. 4, the shaft 116 was separated from the cam 194 by means of bearing 218. By direct connection, rotation of the cam 194 will effect rotation of shaft 116, and hence needle 122, while at the same time, providing reciprocal motion. Accordingly, it is to be understood that instrument 192 provides reciprocal motion only, while instrument 250 provides both reciprocal and rotary motion.

Figure 11:
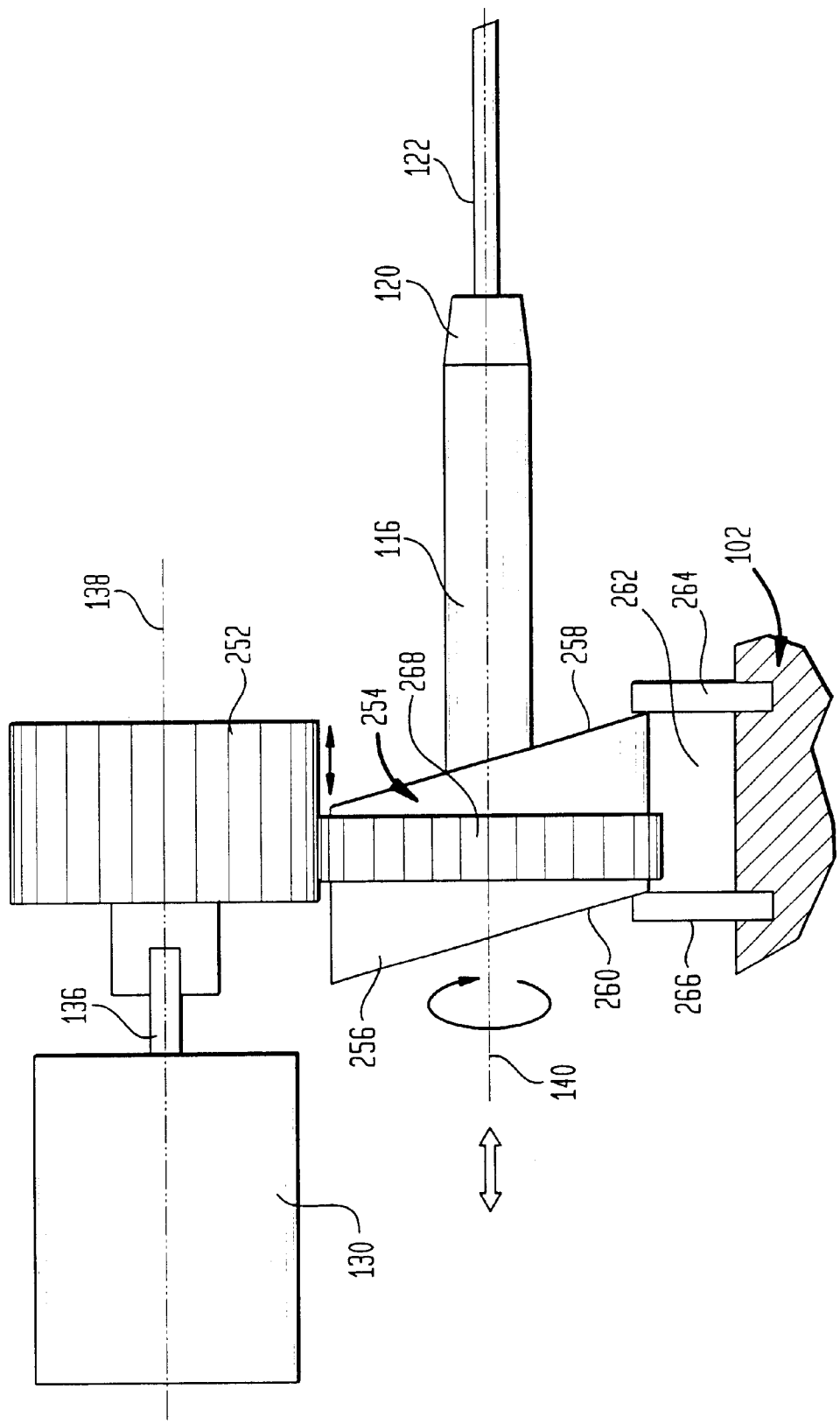
FIG. 11 is a diagrammatic illustration of a needle biopsy instrument constructed in accordance with still another embodiment of the present invention.

Referring now to FIG. 11, a needle biopsy instrument 252 in accordance with another embodiment of the present invention will now be described which provides both rotary and reciprocal motion to the needle 122. A drive gear 252 is coupled to the shaft 136 of the motor 130. As shown, the rotational axis 138 of the drive gear 252 is arranged parallel to, and spaced apart, from the rotational and reciprocal axis 140 of shaft 116. Shaft 116 is attached centrally to cam 254. Cam 254 is constructed from a body 256 having two outwardly facing first and second cam profiles 258, 260. The peripheral edge of the cam 254 is received within an opening 262 formed between two spaced apart pins or cam followers 264, 266. The cam followers 264, 266 are fixedly mounted to an interior portion of the housing 102. A gear 268 is attached circumferentially about cam 254. The cam 254 is positioned such that the gear 268 is arranged in meshed engagement with drive gear 252. As shown, the rotational axis of the gear 268 is arranged parallel to the rotational axis of drive gear 252. Rotation of drive gear 252 will, in turn, effect rotation of gear 268 and cam 256, and hence, shaft 116. As the cam 256 is rotated, its engagement with cam followers 264, 266 will also cause the cam 256 to reciprocate thereby reciprocating shaft 116 and needle 122. The reciprocal motion of the cam 254 is accommodated by gear 268 sliding in meshed engagement with the drive gear 252. If rotational motion of the shaft 116 is not desired, the shaft can be supported by the cam 256 using a bearing 218 in a similar arrangement as shown in the instrument 192 illustrated in FIG. 4.

Figure 13:
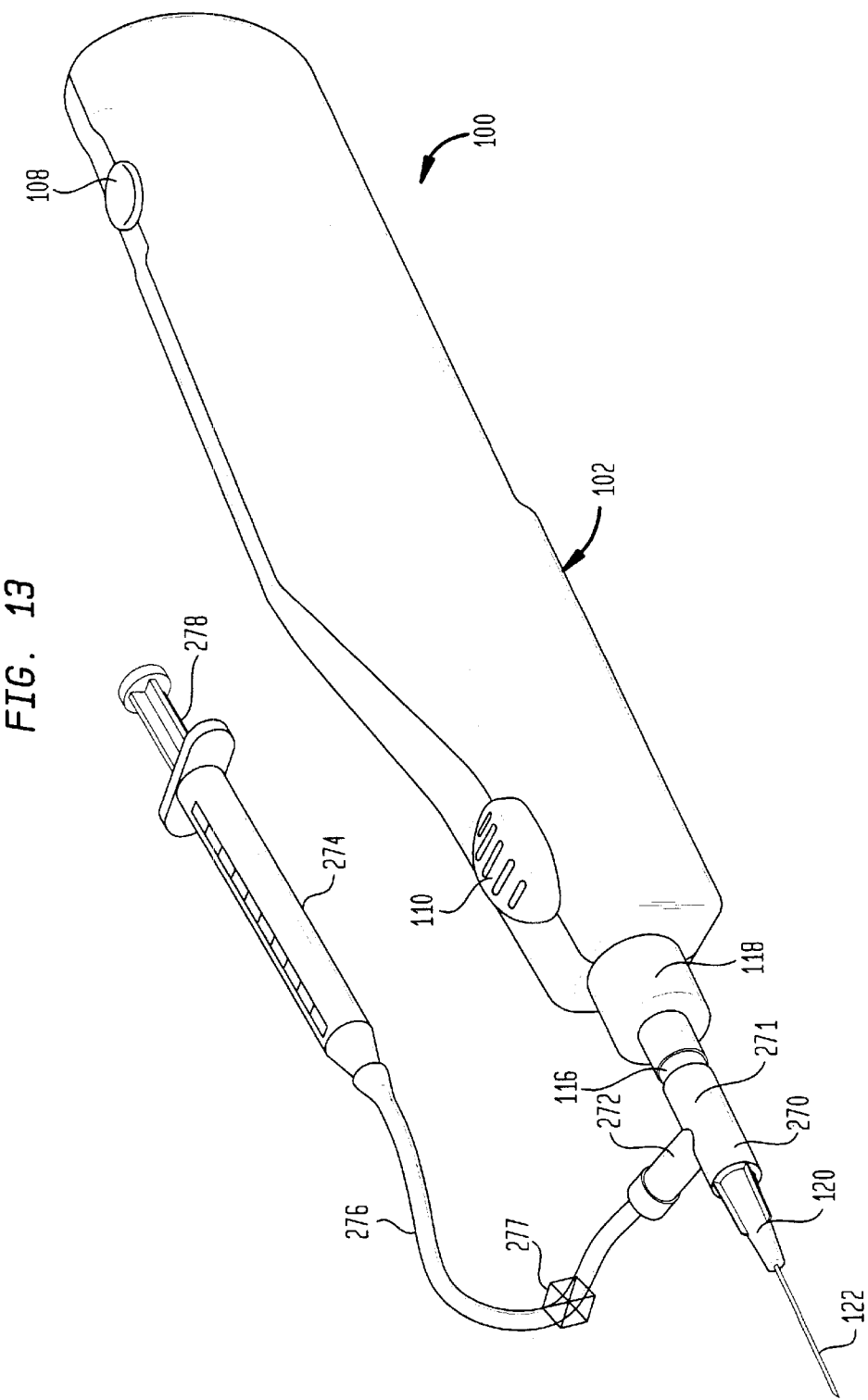
FIG. 13 is a perspective view of the needle biopsy instrument connected to a vacuum source for collecting tissue samples during the biopsy procedure.

The biopsy needle instrument of the present invention provides for reciprocal and/or rotary motion of a needle under programmed control during the biopsy procedure. It may be desirable to couple the biopsy needle instrument with a source of vacuum for aspiration of the tissue sample into needle 122. By way of example, as shown in FIG. 13, a T-connector 270 is attached between the shaft 116 and coupling device 120 which is formed as part of the needle 122. The near end 271 of the T-connector 270 which is attached to the instrument 100 is closed off. Branch 272 of the T-connector 270 is connected to a conventional syringe 274 by means of flexible tubing 276 having an on/off valve 277. While a tissue sample is being collected in the needle 122, plunger 278 can be withdrawn from within the syringe 274 to create vacuum within the T-shaped connector 270, which vacuum is maintained by closing on/off valve 277. This, in turn, will draw the tissue sample into the needle 122 which is now under vacuum. After the predetermined sampling cycle is completed the vacuum is released by opening the on/off valve 277, the needle 122 is removed from the patient's body and the tissue sample can then be dispensed from the need by means of advancing the plunger 278 of the syringe 274.

Figure 14:
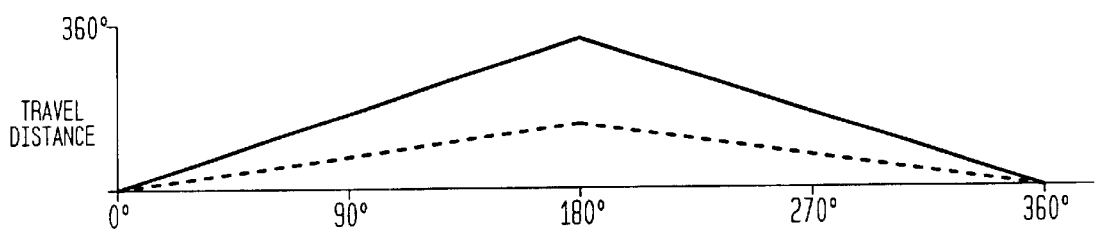
FIG. 14 is a graph illustrating the needle travel displacement for one revolution of the cam constructed in accordance with one embodiment of the present invention.

Referring to FIG. 14, there is graphically illustrated displacement or thrust distance of the needle 122 in relationship to one revolution of cam 156, 254 or cam track 202. As shown, the maximum extended travel or displacement of the needle 122 occurs at 180° of rotation of the cam or cam track. By altering the angular relationship between cam axis 172 and its rotational axis which corresponds to axis 138, see FIG. 3A, the travel distance of the needle 122 can be changed. This is represented by the solid line and dashed line curves in FIG. 14.

Figure 15:
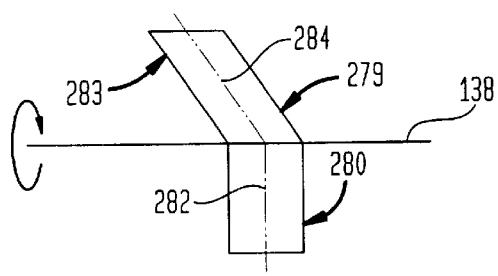
FIG. 15 is a profile of a cam constructed in accordance with another embodiment of the present invention.
Figure 16:
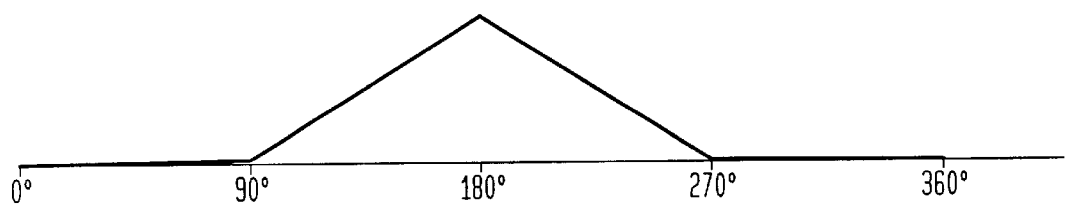
FIG. 16 is a graph illustrating the needle travel displacement for one revolution of the cam as shown in FIG. 15 in accordance with another embodiment of the present invention.

Another embodiment of a cam 279 is shown in FIG. 15. The cam 279 has one segment 280 extending 180° having its axis 282 perpendicular to axis 138. Another equal segment 283 has its axis 284 at an angle to axis 138. The cam 279 provides the needle travel distance profile as shown in FIG. 16. The travel distance provides a dwell period of 90° before and after movement of the needle 122 during rotation of the cam 279.

Figure 17:
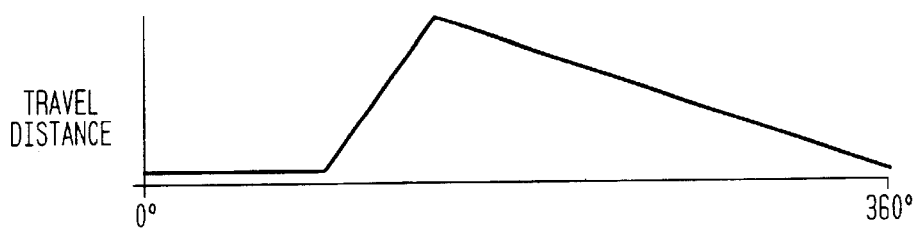
FIG. 17 is a graph illustrating the needle travel displacement for one revolution of a cam constructed in accordance with another embodiment of the present invention.
Figure 18:
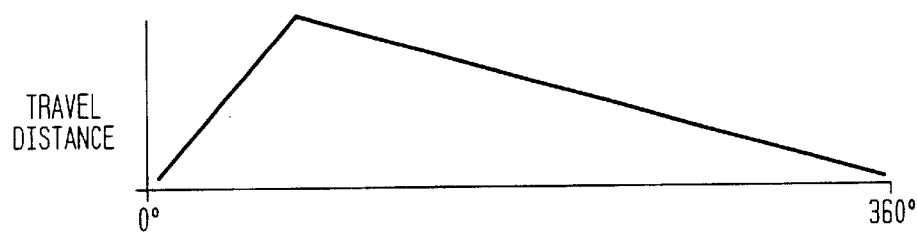
FIG. 18 is a graph illustrating the needle travel displacement for one revolution of a cam constructed in accordance with still another embodiment of the present invention.
Figure 19:
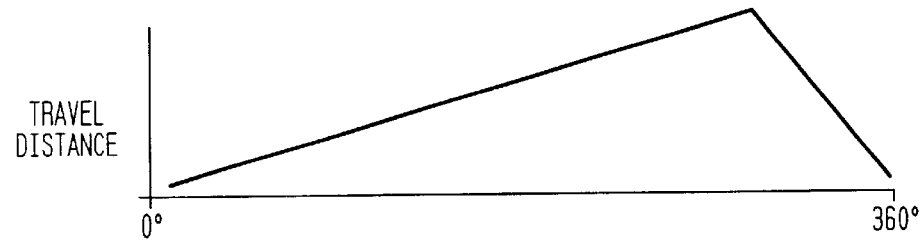
FIG. 19 is a graph illustrating the needle travel displacement for one revolution of the cam constructed in accordance with yet still another embodiment of the present invention.

Using the foregoing modifications and variations of the cam profiles, various combinations of these cam profiles can produce various motion of the needle 122. As shown in FIG. 17, there is initially provided a dwell period followed by a high velocity extension of the needle 122, followed by a slow retraction of the needle into the instrument housing 102. In FIG. 18, a similar travel of the needle 122 is produced, but without a dwell period. As shown in FIG. 19, the needle 122 will have an initial low velocity extension, followed by a high velocity retraction of the needle into the housing 102. From the foregoing, it should be understood that almost any profile can be achieved with reasonable ramp angles. It is to be noted that the higher the ramp angle, which produces higher needle velocities, there is required more torque from the motor 130. This effect can be dampened by the use of a flywheel.

Figure 20:
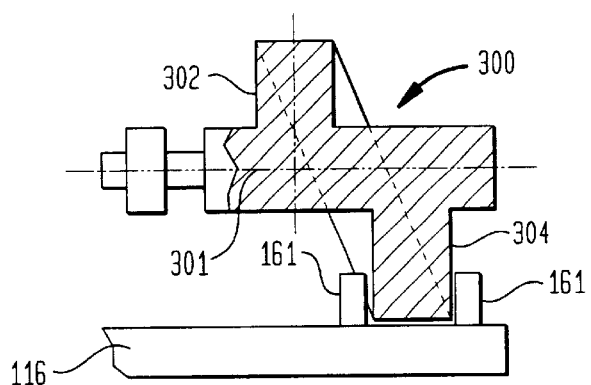
FIG. 20 is a partial cross-sectional view showing the profile of a cam constructed in accordance with another embodiment of the present invention.

Turning to FIG. 20, there is illustrated in cross-section a cam 300 constructed in accordance with another embodiment of the present invention. The cam 300 includes a body 301 which forms a pair of spaced apart outwardly facing cam surfaces 302, 304 for respective engagement with pins 161 which are attached to the shaft 116.

Figure 21:
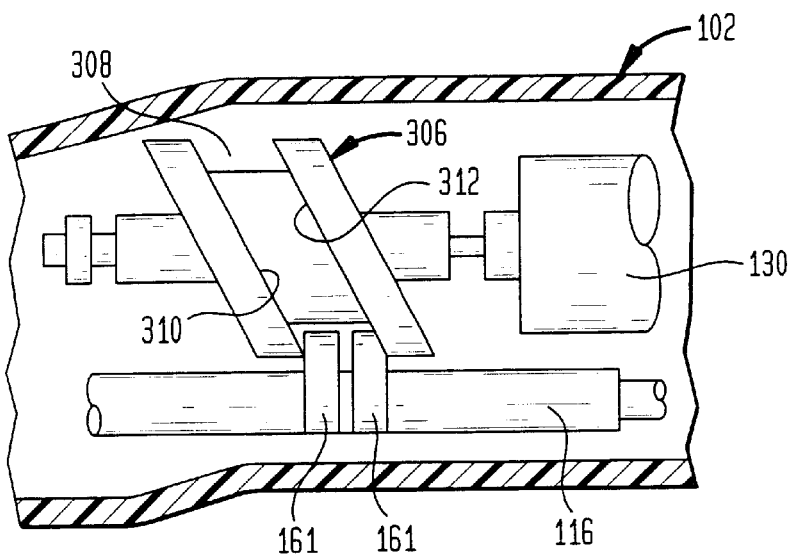
FIG. 21 is a front elevational view showing a cam assembly constructed in accordance with another embodiment of the present invention.
Figure 22:
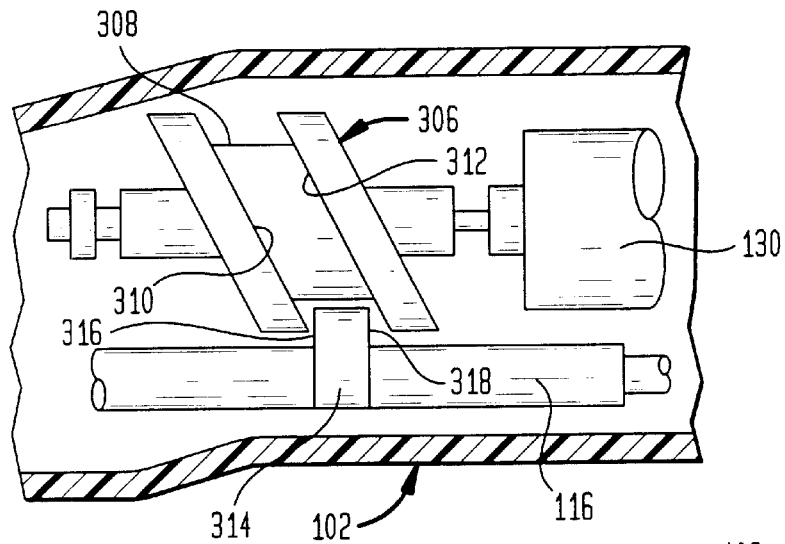
FIG. 22 is a front elevational view showing a cam assembly constructed in accordance with another embodiment of the present invention.
Figure 23:
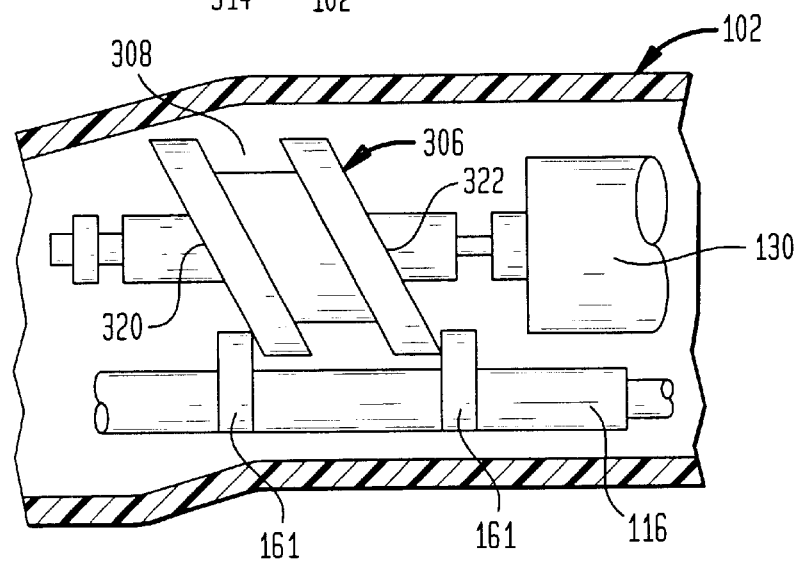
FIG. 23 is a front elevational view showing a cam assembly constructed in accordance with another embodiment of the present invention.

Referring to FIG. 21, cam 306 is provided with a circumscribing recessed portion 308 which is bound by a pair of spaced apart sloping cam surfaces 310, 312. A pair of spaced apart pins 161 attached to shaft 116 extend upwardly into the recessed portion 308 for respective engagement with the cam surfaces 310, 312. As shown in FIG. 22, a single cam follower 314 may be received within the recessed portion 308. The cam follower 314 has outwardly facing spaced apart surfaces 316, 318 for respective engagement with cam surfaces 310, 312. As shown in FIG. 23, the cam 306 is provided with outwardly facing spaced apart sloping cam surfaces 320, 322 for respective engagement with spaced apart pins 161.

Figure 24:
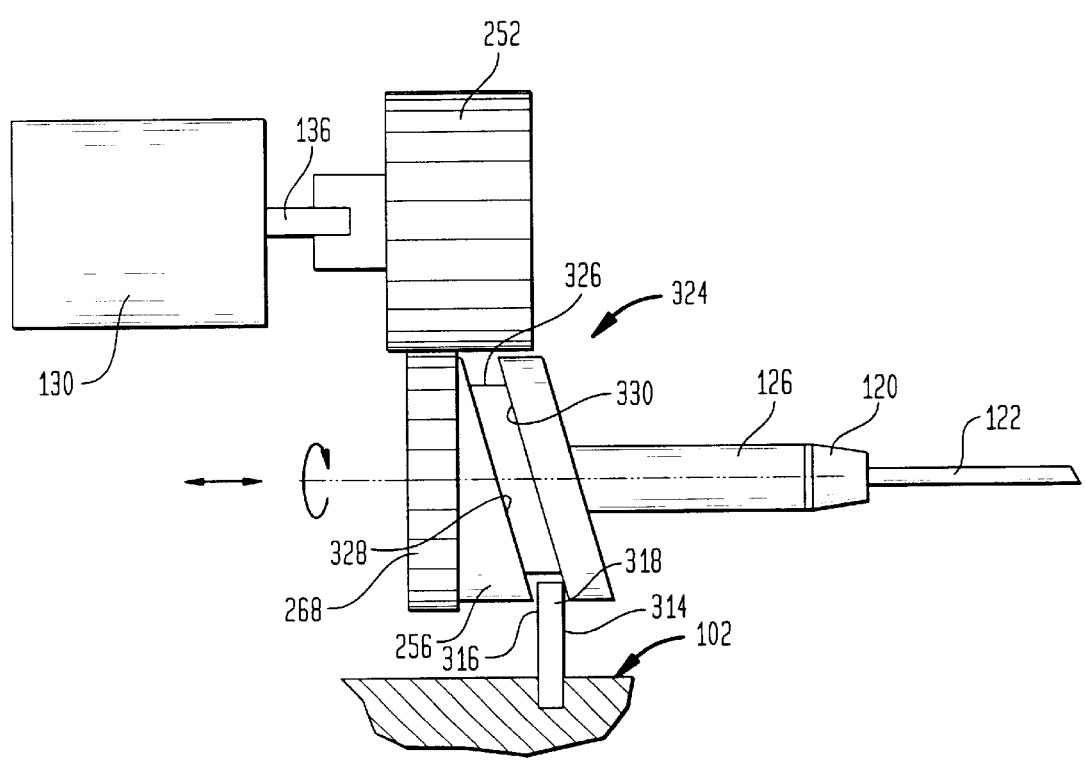
FIG. 24 is a front elevational view showing a cam assembly constructed in accordance with another embodiment of the present invention.

Referring to FIGS. 24–28, various modifications of the drive and cam assembly as shown in FIG. 11 will now be described. In each of these embodiments, the cam assembly will be operative to effect both rotary and reciprocal motion of shaft 116, and hence, needle 122 which is attached thereto. As shown in FIG. 24, the cam assembly 324 includes a gear 268 to which there is attached on one side thereof a cam body 256. The cam body is provided with a circumscribing recessed portion 326 defining a pair of spaced apart sloping cam surfaces 328, 330. A cam follower 314 attached to the housing 102 extends into the recessed portion 326 for engagement with the cam surfaces 328, 330.

Figure 25:
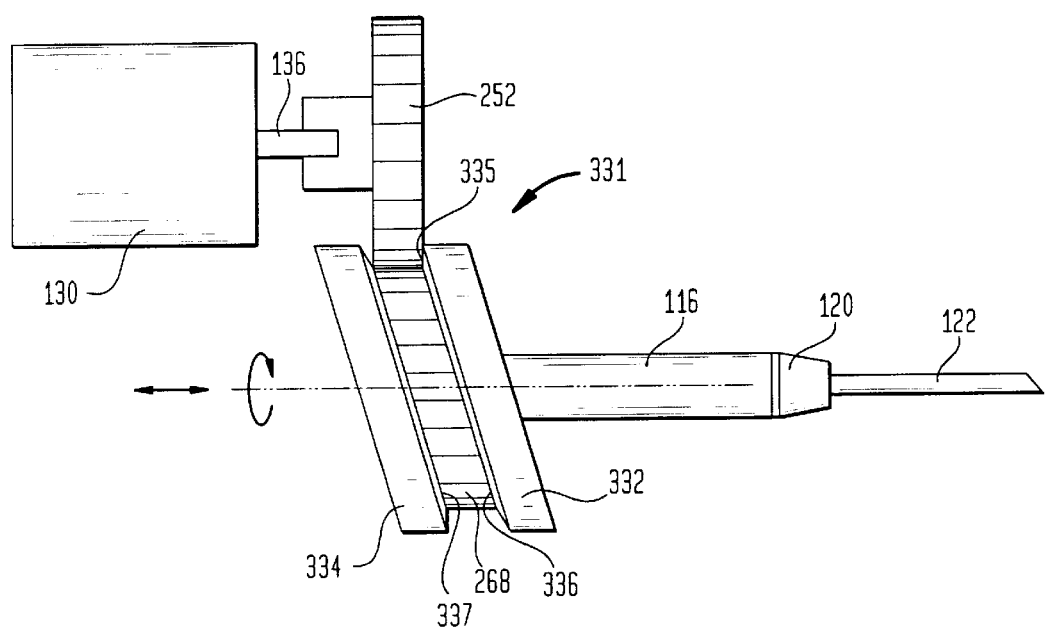
FIG. 25 is a front elevational view showing a cam assembly constructed in accordance with another embodiment of the present invention.

Turning to FIG. 25, the cam assembly 331 includes gear 268 provided with cam bodies 332, 334 supported on either side of the gear. A circumscribing recessed portion 335 defined by the diameter of gear 268 and larger diameters of the cam bodies 332, 334, also define a pair of spaced apart sloping cam surfaces 336, 337. In accordance with this arrangement, drive gear 252 by having a peripheral portion received within the recessed portion 335 functions as a cam follower, as well as effecting rotation of gear 268 as a result of the meshed engagement therewith.

Figure 26:
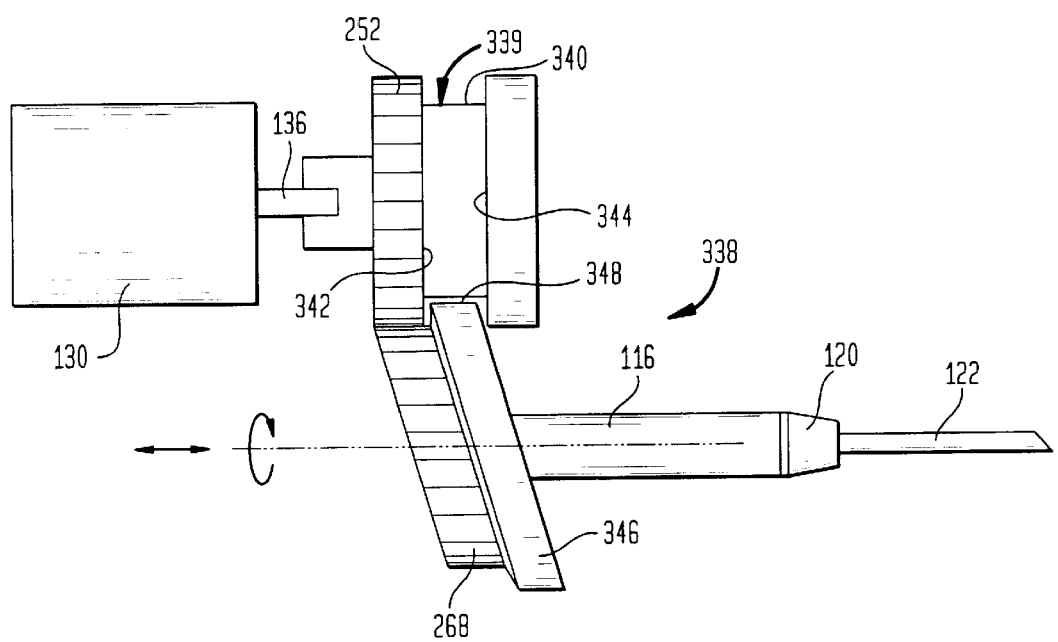
FIG. 26 is a front elevational view showing a cam assembly constructed in accordance with another embodiment of the present invention.

Turning to FIG. 26, the cam assembly 338 includes a cam body 339 having a circumscribing recessed portion 340. The cam body 339 is attached to one surface 342 of drive gear 252. The recessed portion 340 defines a cam surface 344 opposing surface 342 of the drive gear 252 which functions as a second cam surface. A cam follower 346 attached on one side to gear 268, and supporting on its other side shaft 116, has its peripheral portion 348 received within the recessed portion 340. The drive gear 252 is maintained in meshed engagement with gear 268.

Figure 27:
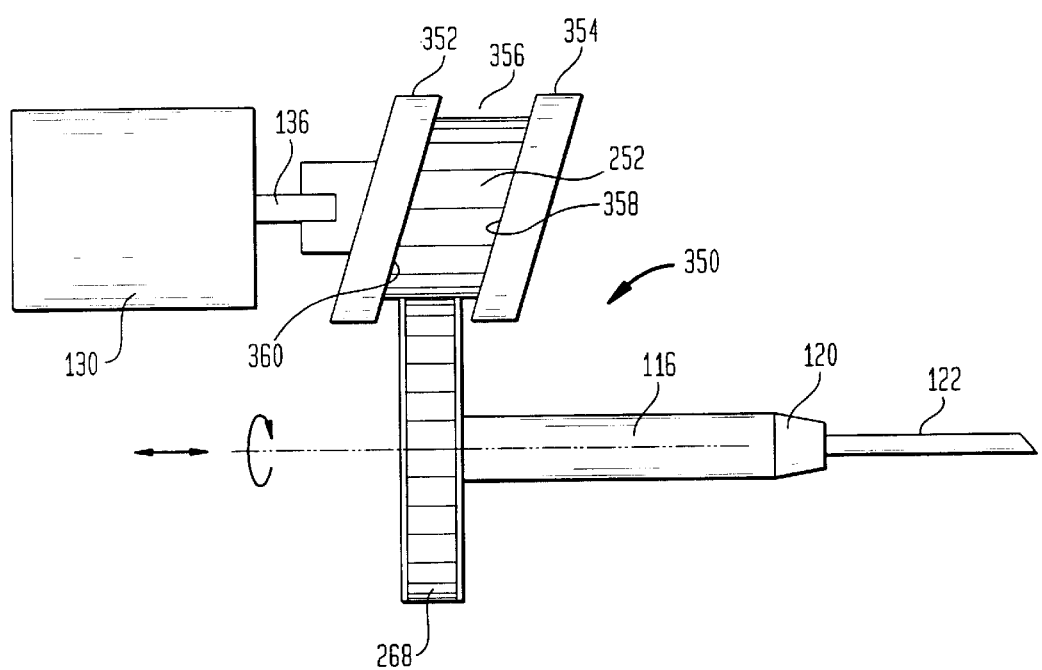
FIG. 27 is a front elevational view showing a cam assembly constructed in accordance with another embodiment of the present invention.

Turning to FIG. 27, the cam assembly 350 includes drive gear 252 provided with cam bodies 352, 354 supported on either side of the drive gear. A circumscribing recessed portion 356 defined by the diameter of the drive gear 252 and the larger diameters of the cam bodies 352, 354, also define a pair of spaced apart sloping cam surfaces 358, 360. In accordance with this arrangement, gear 268 by having a peripheral portion received within the recessed portion 356 functions as a cam follower, as well as effecting rotation of shaft 116 as a result of the meshed engagement with the drive gear 252.

Figure 28:
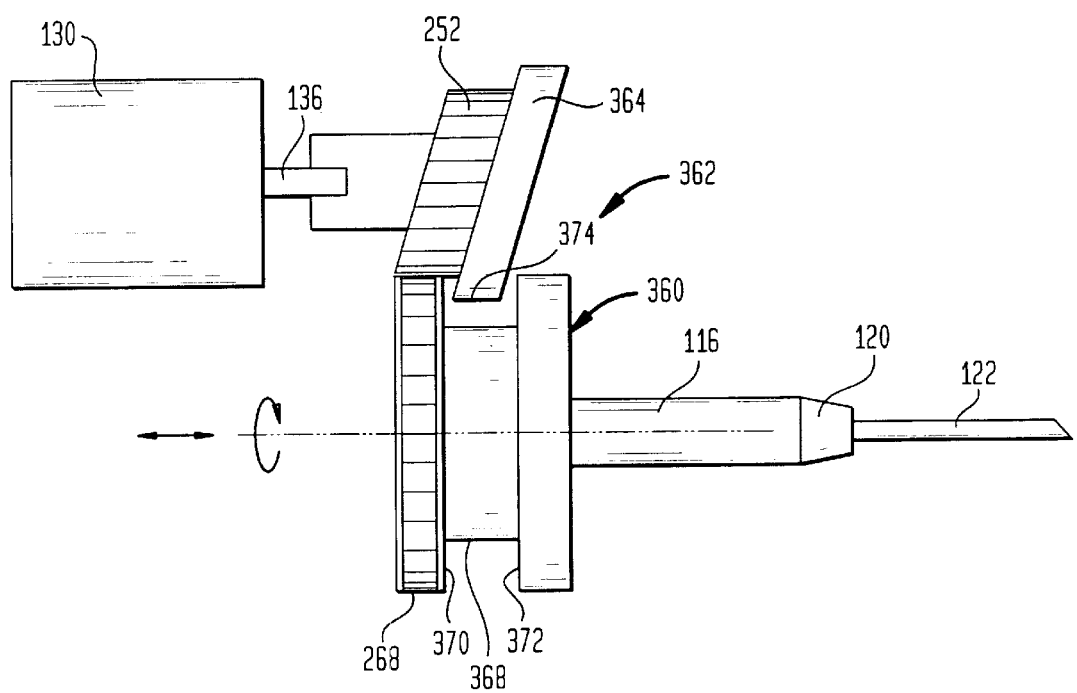
FIG. 28 is a front elevational view showing a cam assembly constructed in accordance with another embodiment of the present invention.

Turning to FIG. 28, the cam assembly 362 includes a cam follower 264 attached to one side of drive gear 252. A cam body 366 having a circumscribing recessed portion 368 is attached to one surface 370 of gear 268. The recessed portion 368 defines a cam surface 372 opposing surface 370 of gear 268 which functions as a second cam surface. The cam follower 364 has a peripheral portion 374 received within the recessed portion 368 for engagement with the cam surfaces 370, 372. The drive gear 252 is maintained in meshed engagement with gear 268 for rotation and reciprocal motion of shaft 116 which is attached to the cam body 366.

Figure 29:
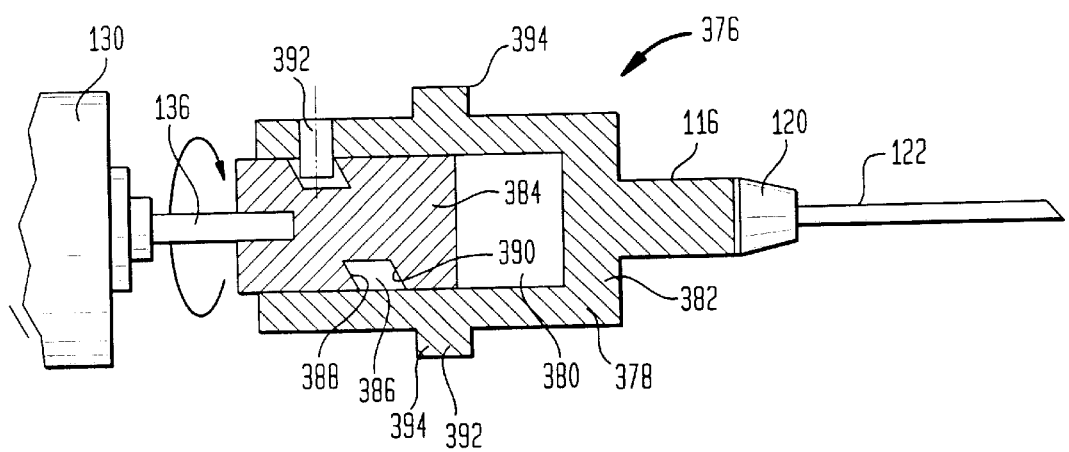
FIG. 29 is a front elevational view showing a cam assembly constructed in accordance with another embodiment of the present invention.
Figure 30:
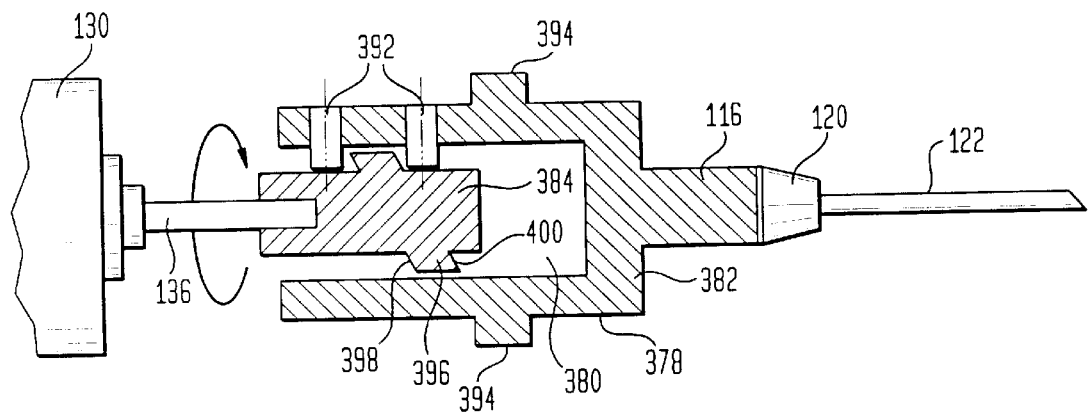
FIG. 30 is a front elevational view showing a cam assembly constructed in accordance with another embodiment of the present invention.

Referring to FIGS. 29 and 30, the cam assemblies are operative for effecting only reciprocal motion of shaft 116, and hence the needle 122. Referring to FIG. 29, the cam assembly 376 includes a cylindrical body 378 having an internal bore 380 opening at one end thereof. The other end is closed by wall 382 from which there extends shaft 116. The bore 380 is circular in shape so as to rotatably receive a circular shaped cam body 384 which is attached to shaft 136 for rotation by means of motor 130. The cam body 384 has a circumscribing recessed portion 386 defining a pair of spaced apart sloping cam surfaces 388, 390. A cam follower 392 in the nature of a pin is attached to the body 378 and extends inwardly so as to be captured within the recessed portion 386.

By rotation of cam body 384, the cylindrical body 378 will reciprocate within the instrument 100. To prevent rotation of the cylindrical body 378, at least one, and preferably a pair of opposing pins 394 extend outwardly from the body 378. The pins 394 are received within longitudinal slots (not shown) formed within the housing 102. In an alternate embodiment, the slots can be helical in nature, which will impart rotary motion to the cylindrical body 378, and hence to the needle 122.

Referring to FIG. 30, the cam body 384 is provided with a pair of spaced apart regions of reduced diameter so as to form an outwardly extending circumscribing cam 396 forming a pair of spaced apart cam surfaces 398, 400. The cam surfaces 398, 400 are respectively engaged by pins 392 extending from the cylindrical body 378.

Although the invention herein has been described with reference to particular embodiments, it is to be understood that the embodiments are merely illustrative of the principles and application of the present invention. For example, by suitable means such as cams and other mechanical assemblies known in the art, the end of the reciprocal shaft 116, and hence the needle 122, can be made to orbit or follow a zigzag or other predetermined path during the thrust of the needle as thus far described. It is therefore to be understood that numerous modifications may be made to the embodiments and that other arrangements may be devised without departing from the spirit and scope of the present invention as defined by the claims.

What is claimed is:

1. An automatic fine needle biopsy instrument for collecting a tissue sample comprising a housing having an opening at one end thereof; a first shaft within said housing for reciprocal motion, said first shaft having a front section and a rear section, said front section of said shaft extending adjacent said opening in said housing; a biopsy needle releasably attached to said first shaft, said biopsy needle having a tip, having an opening; a cam assembly within said housing, said cam assembly comprising first and second cam followers arranged in spaced apart relationship on said first shaft, a cam arranged between said first and second cam followers mounted on a rotatable second shaft, said cam having outwardly facing first and second cam profiles respectively engaging an opposing one of said first and second cam followers, said cam assembly upon rotation of said cam converting rotating motion of said second shaft to reciprocal motion of said first shaft and said biopsy needle whereby said opening of said tip is operative for collecting said tissue sample.

2. The instrument as claimed in claim 1, wherein said first shaft is arranged along a first axis and said second shaft is arranged along a second axis parallel to said first axis.

3. The instrument as claimed in claim 1, further including a motor coupled to said second shaft for rotation thereof.

4. The instrument as claimed in claim 1, wherein said first and second cam profiles are symmetrical.

5. The instrument as claimed in claim 1, wherein said first and second cam profiles are non-symmetrical.

6. The instrument as claimed in claim 1, wherein said cam comprises a cylindrical body having first and second spaced apart surfaces respectively providing said first and second cam profiles.

7. The instrument as claimed in claim 1, further including a coupling device attached to said front section of said first shaft extending outwardly of said housing, said coupling device operative for releasable attachment of a needle thereto.

8. The instrument as claimed in claim 7, further including a needle attached to said coupling device.

9. The instrument as claimed in claim 1, further including a connector having a closed end attached to said front section of said first shaft outwardly of said housing, said connector operative for attachment of a vacuum source thereto.

10. The instrument as claimed in claim 9, further including a needle releasably coupled to said connector.

11. The instrument as claimed in claim 1, further including electronic control means for controlling the operation of said instrument.

12. An automatic fine needle biopsy instrument for collecting a tissue sample comprising a housing having an opening at one end thereof; a reciprocating shaft within said housing, said reciprocating shaft having a front section and a rear section, said front section of said reciprocating shaft extending outwardly through said opening; a biopsy needle releasably attached to said first shaft, said biopsy needle having a tip, having an opening; a cam assembly within said housing operatively coupled to said reciprocating shaft, said cam assembly comprising a cam having first and second spaced apart outwardly facing cam profiles, a first cam follower on one side of said cam in engagement with said first cam profile, and a second cam follower on the other side of said cam in engagement with said second cam profile; and a motor operatively coupled to said cam for rotational movement of said cam, said engagement of said first and second cam profiles with said first and second cam followers during rotation of said cam causing reciprocal movement of said reciprocating shaft and said biopsy needle whereby said opening of said tip is operative for collecting said tissue sample.

13. The instrument as claimed in claim 12, wherein said first and second cam followers are mounted to said reciprocating shaft.

14. The instrument as claimed in claim 13, wherein said cam is mounted on a rotatable shaft within said housing.

15. The instrument as claimed in claim 14, wherein said motor within said housing is coupled to said rotatable shaft for rotation thereof.

16. The instrument as claimed in claim 12, further including a needle attached to said front section of said reciprocating shaft outwardly of said housing.

17. The instrument as claimed in claim 16, further including a coupling device for releasably coupling said needle to said reciprocating shaft.

18. The instrument as claimed in claim 12, wherein said first and second cam followers are fixedly attached to said housing on opposite sides of said cam.

19. The instrument as claimed in claim 18, wherein said cam is mounted on said reciprocating shaft.

20. The instrument as claimed in claim 19, wherein said motor includes a shaft having an axis parallel to an axis of said reciprocating shaft.

21. The instrument as claimed in claim 19, further including a first gear within said housing rotatable by operation of said motor, and a second gear arranged circumferentially about said cam, said first and second gears being in sliding meshed engagement, whereby rotation of said first gear causes rotation of said cam for rotation of said reciprocating shaft, and the engagement of said first and second cam followers with said cam causing reciprocating movement of said reciprocating shaft.

22. The instrument as claimed in claim 21, wherein said cam has an axis of rotation colinear with an axis of rotation of said reciprocating shaft and parallel to an axis of rotation of said first gear.

23. The instrument as claimed in claim 12, where said first and second cam profiles control the stroke length of said reciprocating shaft.

24. The instrument as claimed in claim 12, further including a needle attached to said front section of said shaft outwardly of said housing, and means for creating a vacuum in said needle.

25. The instrument as claimed in claim 12, further including electronic control means for controlling the operation of said instrument.

26. An automatic fine needle biopsy instrument for collecting a tissue sample comprising a housing having an opening at one end thereof; a reciprocating shaft along a first axis within said housing, said reciprocating shaft having a front section and a rear section, said front section of the shaft extending outwardly through said opening; a biopsy needle releasably attached to said first shaft, said biopsy needle having a tip, having an opening; a cam assembly within said housing comprising a cam having first and second spaced apart cam profiles, a first cam follower on one side of said cam in engagement with said first cam profile, and a second cam follower on the other side of said cam in engagement with said second cam profile; and a motor on a second axis within said housing operatively coupled to said cam for rotational movement of said cam, said second axis offset from said first axis, rotation of said cam causing reciprocal movement of said reciprocating shaft, and said biopsy needle whereby said open end of said tip is operative for collecting said tissue samples.

27. The instrument as claimed in claim 26, wherein said first and second cam followers are mounted to said reciprocating shaft.

28. The instrument as claimed in claim 27, wherein said cam is mounted on a rotatable shaft within said housing.

29. The instrument as claimed in claim 26, further including a needle attached to said front section of said shaft outwardly of said housing.

30. The instrument as claimed in claim 29, further including a coupling device for releasably coupling said needle to said shaft.

31. The instrument as claimed in claim 26, wherein said first and second cam followers are fixedly attached to said housing on opposite sides of said cam.

32. The instrument as claimed in claim 31, wherein said cam is mounted on said reciprocating shaft.

33. The instrument as claimed in claim 32, further including a motor within said housing operatively coupled to said cam for rotation thereof.

34. The instrument as claimed in claim 33, further including a first gear within said housing rotatable by operation of said motor, and a second gear arranged circumferentially about said cam, said first and second gears being in sliding meshed engagement, whereby rotation of said first gear causes rotation of said cam for rotation of said reciprocating shaft, and the engagement of said first and second cam followers with said cam causing reciprocating movement of said reciprocating shaft.

35. The instrument as claimed in claim 26, wherein said first and second cam profiles are non-symmetrical.

36. The instrument as claimed in claim 26, where said first and second cam profiles control the stroke length of said reciprocating shaft.

37. The instrument as claimed in claim 26, further including a needle attached to said front section of said shaft outwardly of said housing, and means for creating a vacuum in said needle.

38. The instrument as claimed in claim 26, further including electronic control means for controlling the operation of said instrument.

39. An automatic fine needle biopsy instrument for collecting a tissue sample comprising a housing having an opening at one end thereof; a shaft within said housing for reciprocal motion, said shaft having a front section and a rear section, said front section of said shaft extending outwardly through said opening of said housing; a biopsy needle releasably attached to said first shaft, said biopsy needle having a tip, having an opening; a motor within said housing; and a cam assembly within said housing comprising a cam operationally coupled to said motor for rotational movement of said cam, said cam having a track and a cam follower fixed to said housing and received within said track; receipt of said cam within said track during rotation of said cam by said motor causing reciprocal movement of said shaft and said biopsy needle whereby said opening of said tip is operative for collecting said tissue sample.

40. The instrument as claimed in claim 39, further including a coupling attached to said motor and coupled to said cam.

41. The instrument as claimed in claim 40, wherein said cam comprises a body having a bore therein and said coupling sliding received within said bore.

42. The instrument as claimed in claim 41, further including means for preventing relative rotation between said coupling and said cam when said coupling is received within said bore, whereby rotation of said coupling causes rotation of said cam and reciprocal and rotational motion of said shaft.

43. The instrument as claimed in claim 42, wherein said shaft is attached to said cam in longitudinal alignment therewith.

44. The instrument as claimed in claim 39, further including a bearing coupling said shaft to said cam, whereby rotation of said cam causes reciprocal motion of said shaft while said bearing prevents rotational motion of said shaft.

45. The instrument as claimed in claim 39, further including a needle releasably coupled to said shaft outwardly of said housing.

46. The instrument as claimed in claim 45, further including means for creating a vacuum in said needle.

47. The instrument as claimed in claim 39, further including electronic control means for controlling the operation of said instrument.

48. The instrument as claimed in claim 39, wherein said cam assembly controls the stroke length of said shaft.

* * * * *